US012213852B2

(12) United States Patent
Van Der Poel et al.

(10) Patent No.: US 12,213,852 B2
(45) Date of Patent: Feb. 4, 2025

(54) METHOD AND SYSTEM FOR MEASURING PERIODONTAL POCKET DEPTH

(71) Applicant: 3SHAPE A/S, Copenhagen K (DK)

(72) Inventors: Mike Van Der Poel, Rødovre (DK); Astrid Birch, Holte (DK); Michael Vinther, København S (DK); Sonal Sharad Patil, Gentofte (DK); Steen Frost Tofthøj, Værløse (DK)

(73) Assignee: 3SHAPE A/S, Kobenhavn K (DK)

( * ) Notice: Subject to any disclaimer, the term of this patent is extended or adjusted under 35 U.S.C. 154(b) by 948 days.

(21) Appl. No.: 17/289,938

(22) PCT Filed: Oct. 31, 2019

(86) PCT No.: PCT/EP2019/079859
§ 371 (c)(1),
(2) Date: Apr. 29, 2021

(87) PCT Pub. No.: WO2020/089406
PCT Pub. Date: May 7, 2020

(65) Prior Publication Data
US 2022/0008180 A1    Jan. 13, 2022

(30) Foreign Application Priority Data

Nov. 1, 2018 (DK) ................... 2018 70715

(51) Int. Cl.
*A61C 19/04* (2006.01)
*A61B 1/24* (2006.01)
(Continued)

(52) U.S. Cl.
CPC .............. *A61C 19/043* (2013.01); *A61B 1/24* (2013.01); *G06T 7/55* (2017.01); *G06T 2207/30036* (2013.01); *H04N 13/207* (2018.05)

(58) Field of Classification Search
CPC ................... A61C 19/043; G06T 7/55; G06T 2207/30036; A61B 1/24
See application file for complete search history.

(56) References Cited

U.S. PATENT DOCUMENTS 5,897,509 A * 4/1999 Toda ................. A61B 1/24
433/29
5,951,292 A * 9/1999 Lee ................... G01H 1/12
600/589

(Continued)

FOREIGN PATENT DOCUMENTS

CN    101854880 A    10/2010
CN    104955418 A    9/2015

(Continued)

OTHER PUBLICATIONS

Mitrović, U et al., "Simultaneous 3D-2D image registration and C-arm calibration: Application to endovascular image-guided interventions", Medical Physics, vol. 42, No. 11, pp. 6433-6447, Nov. 2015.

(Continued)

*Primary Examiner* — Utpal D Shah
(74) *Attorney, Agent, or Firm* — Buchanan Ingersoll & Rooney PC

(57) ABSTRACT

A system for measuring a depth of a periodontal pocket defined by a gap between a tooth and gingiva includes a frame, one camera, and a processor. The frame is configured to be worn by a user. The camera is configured to capture at least one 2D image of an intraoral target area. The at least one 2D image includes a representation of at least a part of the tooth, a gingiva margin defined by a section of the gingiva adjacent to the at least a part of the tooth, and a probe tip when the probe tip is inserted into the periodontal pocket. The processor is configured to receive the captured at least one 2D image and to determine an insertion length of the (Continued)

probe tip in the periodontal pocket. The determined insertion length represents the depth of the periodontal pocket.

22 Claims, 16 Drawing Sheets

(51) Int. Cl.
*G06T 7/55* (2017.01)
*H04N 13/207* (2018.01)

(56) References Cited

U.S. PATENT DOCUMENTS

| | | | |
|---|---|---|---|
| 8,922,589 B2 | 12/2014 | Laor | |
| 9,454,846 B2* | 9/2016 | Pesach | A61B 1/247 |
| 9,690,119 B2 | 6/2017 | Garofolo et al. | |
| 9,772,495 B2 | 6/2017 | Tam et al. | |
| 9,877,642 B2 | 1/2018 | Duret | |
| 9,967,475 B2 | 5/2018 | Schneider et al. | |
| 10,021,351 B2* | 7/2018 | Jessop | H04N 13/128 |
| 10,032,271 B2 | 7/2018 | Somasundaram et al. | |
| 10,765,358 B2* | 9/2020 | Hussein | A61C 19/04 |
| 11,759,091 B2* | 9/2023 | Duret | A61C 9/0053 |
| 2009/0061383 A1* | 3/2009 | Kang | A61C 19/043 433/72 |
| 2009/0298005 A1* | 12/2009 | Gibbs | A61C 19/043 433/29 |
| 2015/0348320 A1* | 12/2015 | Pesach | A61C 19/043 382/128 |
| 2015/0350517 A1 | 12/2015 | Duret et al. | |
| 2016/0220105 A1* | 8/2016 | Duret | H04N 23/56 |
| 2016/0225192 A1 | 8/2016 | Jones et al. | |
| 2016/0242623 A1 | 8/2016 | Pasini et al. | |
| 2017/0065379 A1 | 3/2017 | Cowburn et al. | |
| 2017/0068119 A1 | 3/2017 | Antaki et al. | |
| 2018/0168780 A1* | 6/2018 | Kopelman | G06V 10/758 |
| 2018/0168781 A1 | 6/2018 | Kopelman et al. | |
| 2020/0155285 A1* | 5/2020 | Pesach | A61B 1/24 |
| 2020/0405154 A1* | 12/2020 | Moghaddam | A61B 5/0035 |

FOREIGN PATENT DOCUMENTS

| | | |
|---|---|---|
| CN | 107529968 A | 1/2018 |
| DE | 102012103970 A1 | 9/2013 |
| EP | 2165674 A1 | 3/2010 |
| ES | 2115544 A1 | 6/1998 |
| GB | 2552257 A | 1/2018 |
| JP | 2015-526930 A | 9/2015 |
| WO | 2013139858 A1 | 9/2013 |
| WO | 2014076045 A2 | 5/2014 |
| WO | 2014102779 A2 | 7/2014 |
| WO | 2016195972 A1 | 12/2016 |
| WO | 2017144934 A1 | 8/2017 |

OTHER PUBLICATIONS

First Office Action issued in corresponding Chinese Patent Application No. 2019800876878, dated Jan. 4, 2022, with English Translation (15 pages).

* cited by examiner

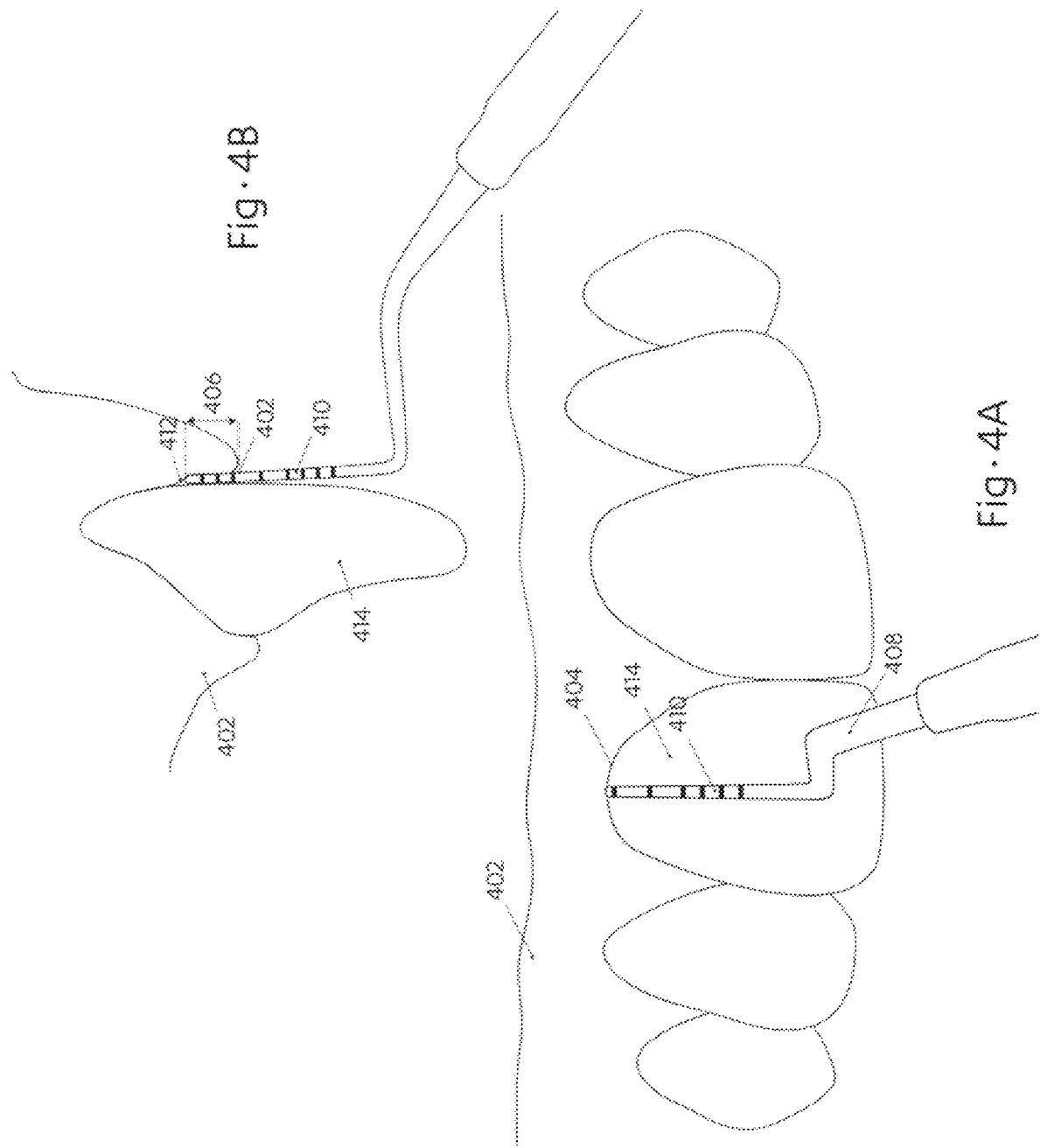

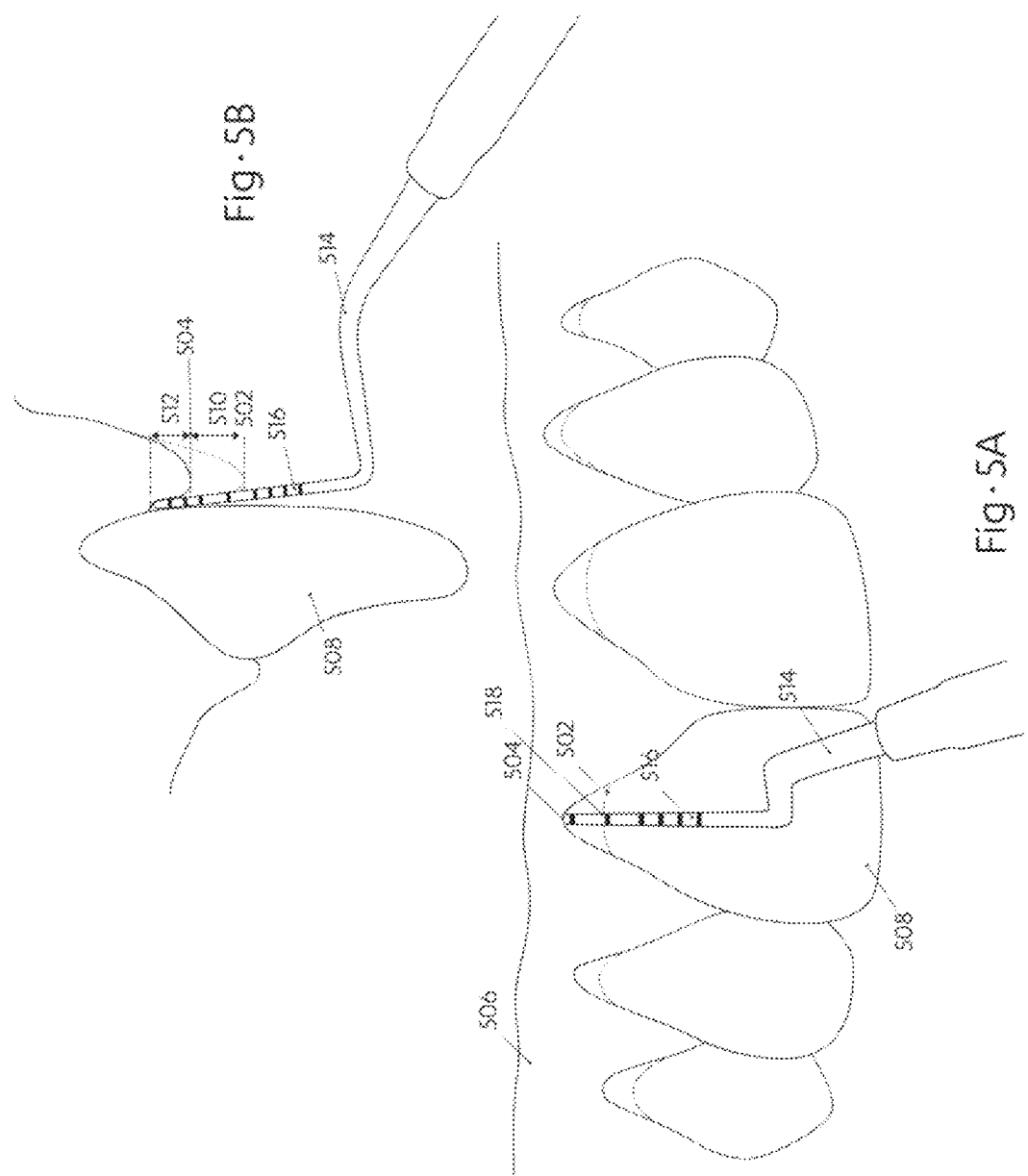

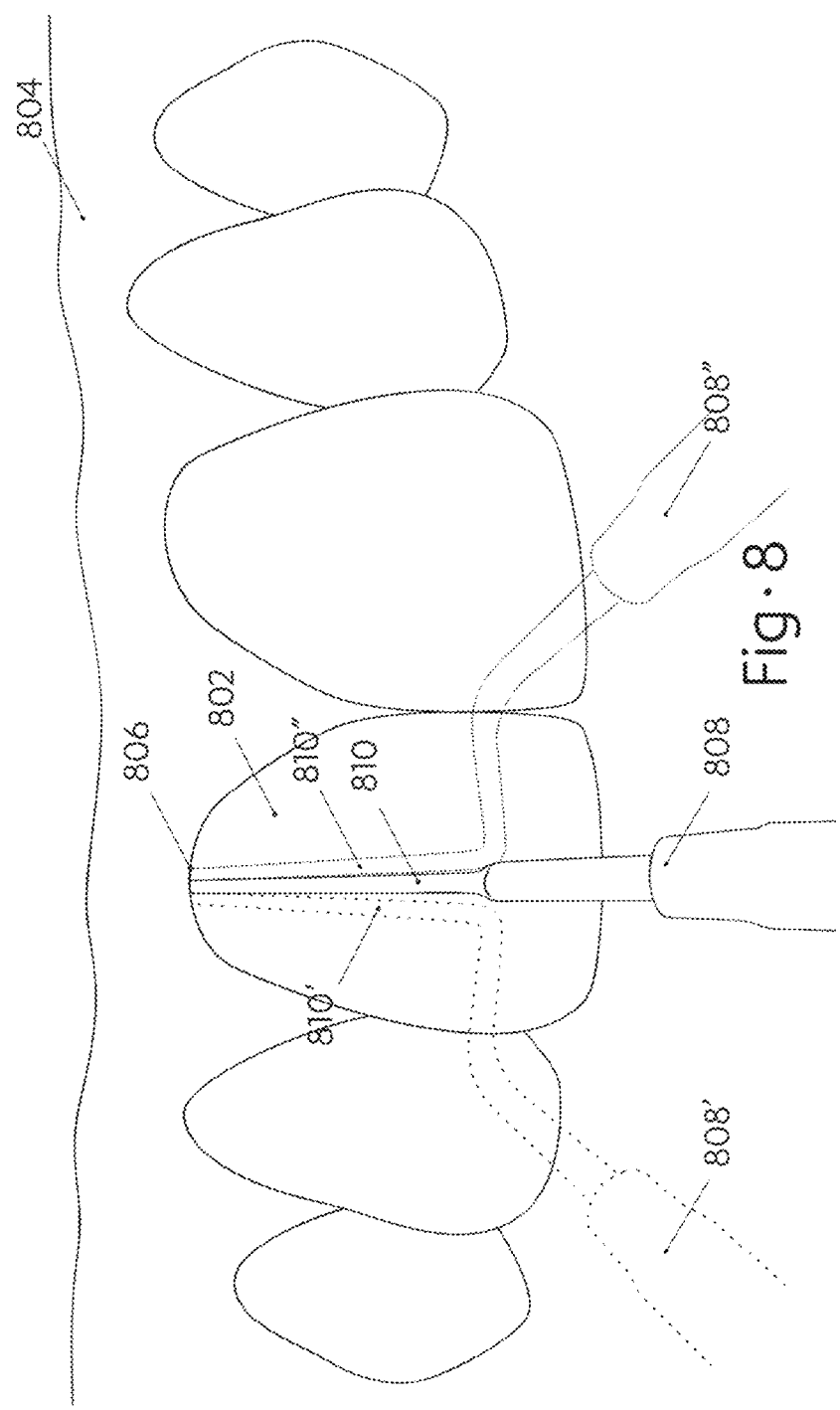

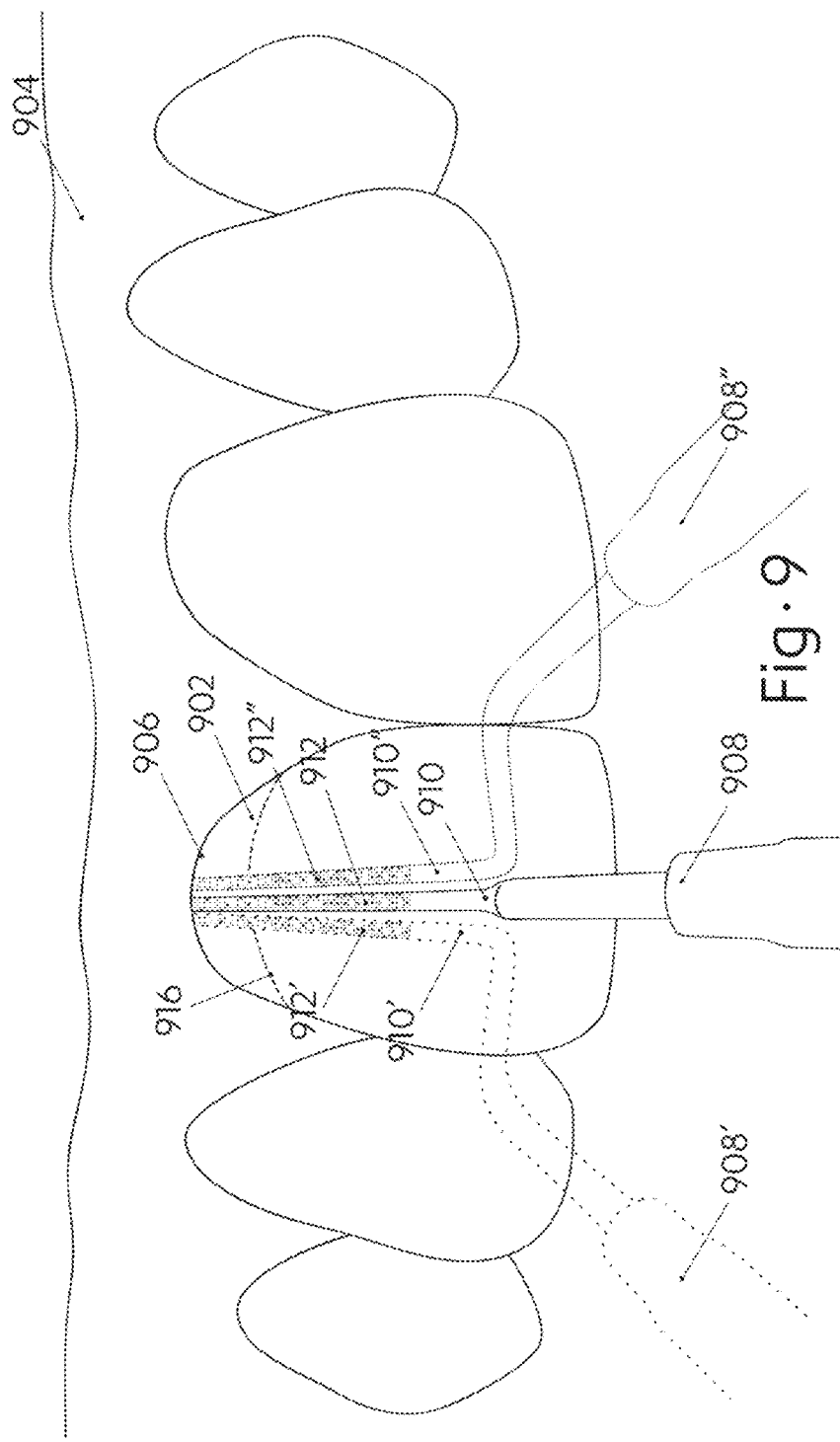

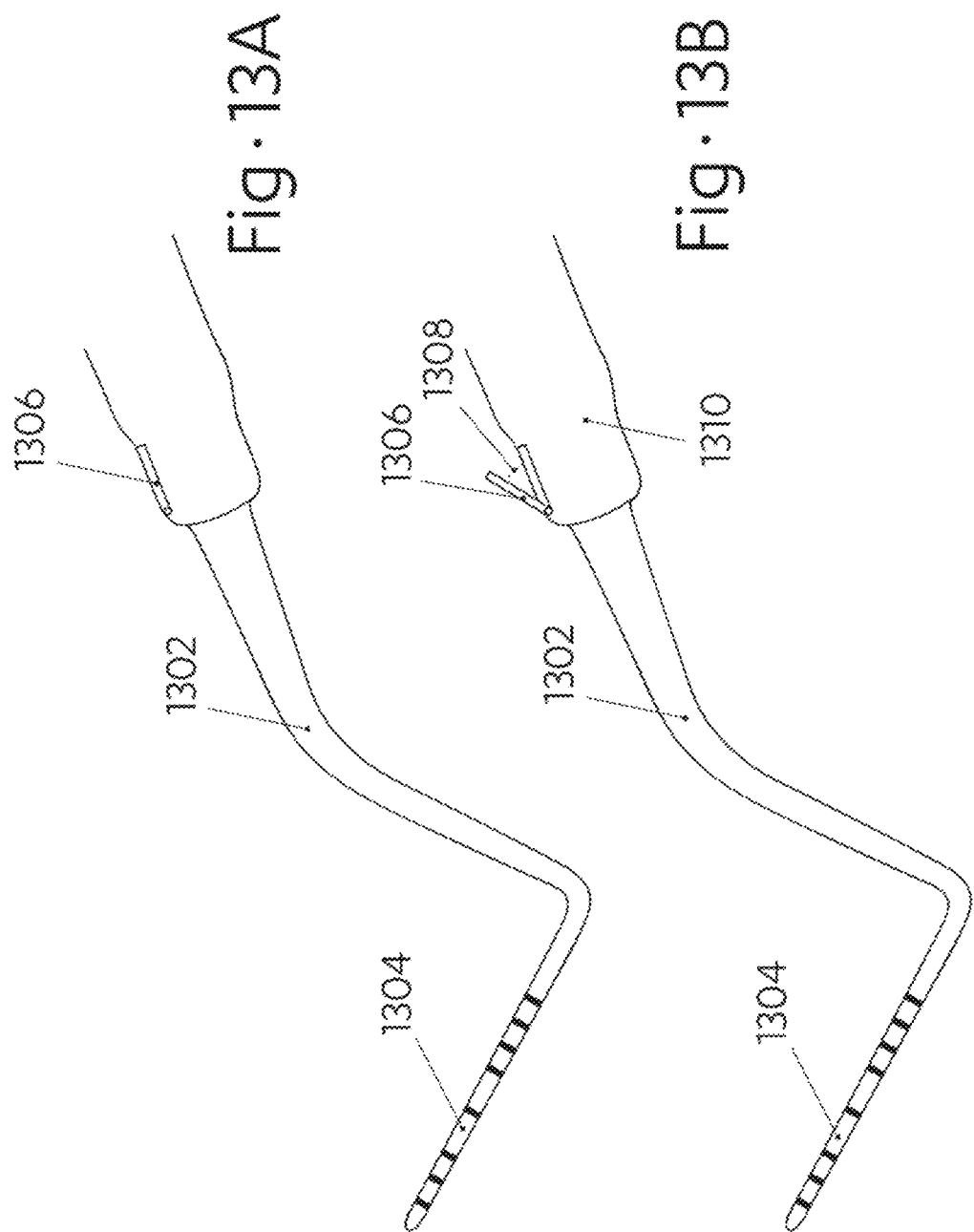

METHOD AND SYSTEM FOR MEASURING PERIODONTAL POCKET DEPTH

TECHNICAL FIELD

The disclosure relates to dental measurements. In particular, the disclosure relates to a method and system for automatically measuring periodontal pocket depth, i.e. depth of a pocket between gingiva and a tooth.

BACKGROUND

The periodontal pocket depth also known as gingival sulcus, is measured from gingiva margin (the top of the gingiva) to the epithelial attachment (the point where the gingiva attaches to the tooth), which forms the bottom of the pocket. The gingival recession is described as apical migration of gingiva margin such that the gingiva margin is gradually displaced away from the cementoenamel junction, thereby exposing the root surface to the oral environment. The gingiva recession is typically measured as a distance between the recessed gingiva and cementoenamel junction. The loss of attachment includes both periodontal pocket depth and gingiva recession measurements. In case of no or substantially no gingiva recession, the loss of attachment is equal to the periodontal pocket depth. However, in case of a gingiva recession, the loss of attachment is a combination of the gingiva recession and periodontal pocket depth. Measurement of pocket depth is a primary method for detecting periodontal (gum) disease, which is a chronic inflammatory disease of periodontium and is the main cause of tooth loss.

As periodontal disease progresses, the pockets become larger and are filled with bacteria and pus, and in time, destruction of the tissue attachment to the teeth and destruction of the supporting bone structure occurs. Periodontal disease is usually painless, site specific and goes through periods of exacerbation and remission.

In order to measure the periodontal pocket depth, a periodontal probe is generally used by dentists. The standard periodontal probes include either graduations or other marks on the probe tip to indicate the depth which the probe tip penetrates between the tooth and gingiva. Other periodontal probe designs may include color-coded regions on the probe tip as a time saving measure which allows a dentist to more quickly differentiate healthy teeth from unhealthy teeth.

A significant shortcoming of the previously discussed periodontal probes involves the difficulty encountered by the dentist in reading the color-coding or graduations once the probe is in position between the tooth and gingiva. Overhead dental lights may be used but such arrangement provide insufficient illumination for the accurate and quick reading of the colors and graduations present on the probe tip of a periodontal probe. Furthermore, the depth measurement may also be influenced by the force that is applied on the probe tip when the probe tip is inserted into the pocket, thus making such measurements dependent upon user's skills and experience. Lastly, the depth measurements may have to be manually entered in a patient record. Such manual entry not only makes the process time consuming and cumbersome but also prone to human error.

Therefore, an accurate and easy to use solution to measure and record periodontal pocket depth is needed in the dental field.

SUMMARY

According to an embodiment, a system for measuring a depth of a periodontal pocket is disclosed. The system includes at least a frame, at least one camera, and a processor. The frame is configured to be worn by a user. The at least one camera is attached to the frame and configured to capture at least one 2D image of an intraoral target area. The at least one 2D image includes a representation of at least a part of the tooth, a gingiva margin defined by a section of the gingiva adjacent to the at least a part of the tooth, and a probe tip when the probe tip is inserted into the periodontal pocket. The processor is configured to receive the captured at least one 2D image. The processor is further configured to determine, in relation to the gingiva margin, an insertion length of the probe tip in the periodontal pocket by applying an image processing technique on information obtained about the probe tip in the captured at least one 2D image. The determined insertion length represents the depth of the periodontal pocket. Having the at least one camera attached to a wearable frame is particularly useful because the at least one camera captures a real time image data including the at least one 2D image that represents what the user would see using a conventional digital loupe system but with the use of the processor, the periodontal pocket depth is automatically determined and may also be automatically recorded in patient's record. In addition, a specific arrangement of the camera on the frame allows the user to maintain an ergonomically proper posture while the at least one camera captures the real time image data.

The system, which may be a digital dental loupe system, disclosed in this embodiment is configured to include one or more of the embodiments that are disclosed later.

According to another embodiment, a system is disclosed. The loupe system includes a frame, at least one camera, and a processor. The frame is configured to be worn by a user. The at least one camera is attached to the frame and configured to capture at least one 2D image of the intraoral target area. The processor is configured to receive the captured at least one 2D image. The processor is further configured to process the captured at least one 2D image of the intraoral target area. The system, which may be a digital dental loupe system, disclosed in this embodiment is configured to include one or more of the embodiments that are disclosed later. Although following embodiments of the disclosure are described in relation to a periodontal probe but the skilled person would appreciate that many of these embodiments may be implemented with a dental instrument other than the periodontal probe and such combination are within the scope of this disclosure. For example, the dental instrument like a mouth mirror may be identified in the at least one 2D image, the dental instrument may include fiducial markers that facilitates in identifying the dental instrument and also its orientation, the dental instrument may be correlated to a digital profile stored in a memory. The skilled person would appreciate that embodiments that are not recited specifically for pocket depth measurements may be used in combination with the dental instrument.

In one embodiment, the at least one camera is configured to include a fixed focus with a focus set for a predetermined distance range from the at least one camera such as between 30 cm to 60 cm, preferably between 45 cm to 55 cm, and most preferably between 40 cm to 50 cm. In another embodiment, the at least one camera includes a focus module that is configured to through user manual input or automatically focus the at least one camera at a specific distance range from the at least one camera. The specific distance range preferably spans along patient's oral cavity. Such focus adjustment may be either continuous or stepped in discrete steps with each step having a different or at least partially overlapping distance range. The specific distance range from the at least one camera may be between 30 cm to 60 cm, preferably between 45 cm to 55 cm, and most preferably between 40 cm to 50 cm. The focus module may include adjustment, resulting in the specific distance range, that allows for changing the focal length of the lens component included in the at least one camera.

The disclosed system, in several embodiments, may utilize a real time image data that includes a sequence of 2D images, which comprises the at least one 2D image. The real time image data may include a video sequence of the intraoral target area, the at least one 2D image may be extracted from the video sequence. The camera is configured to capture the sequence of 2D images/video sequence and the processor is configured to receive the sequence of 2D images/video sequence and to extract the at least one 2D image from the sequence of 2D images/video sequence. Thus, the capturing of the at least one 2D image may include at least one camera being configured to extract the at least one 2D image from the sequence of 2D images/video sequence and/or capturing the at least one 2D image directly from the intraoral target area.

In an embodiment, the processor is configured to automatically apply adjustments to the real time image data. Such adjustments may include changing one of the brightness, contrast, gamma values, or color space. This will allow for improving perception. Such adjustment may be at global level on the image or to a part of the image, such on a region of interest like probe, etc.

In an embodiment, the intraoral target area includes at least i) a part of the tooth, ii) a gingiva margin defined by a section of the gingiva adjacent to the at least a part of the tooth, and iii) a probe tip when the probe tip is inserted into the periodontal pocket. In another embodiment, the intraoral target area includes at least i) a part of the tooth, ii) a cementoenamel junction adjacent to the at least a part of the tooth, and iii) a probe tip when the probe tip is inserted into the periodontal pocket. In any of these embodiments, the intraoral target area may further include the entire tooth for which periodontal pocket is to be measured and even other parts of the intraoral cavity such as teeth neighboring to the tooth, gingiva surrounding the tooth and the neighboring teeth with or without gingiva adjacent to such neighboring teeth. The intraoral target area may further include parts of the periodontal probe other than the probe tip, for example a probe element that is configured to deviate to show variation when a predefined insertion force on the probe tip is applied. The intraoral target area may also include entire dental arch and other organs of the oral cavity including restorations like crowns, bridges, etc.

In different embodiments, where no or substantially no gingival recession is present or where gingival recession has not occurred, the insertion length necessarily represents the periodontal pocket depth, i.e. the periodontal pocket depth is equal to the insertion length. In a first embodiment, the gingiva margin is at least substantially aligned with the cementoenamel junction and the processor is configured to determine the pocket depth in relation to the gingiva margin by determining the insertion length. The determination of the insertion length may be performed in accordance with any of the embodiments included in this disclosure. Thus, with no or substantially no gingival recession, the loss of attachment is equal to the determined pocket depth. In a second embodiment where a gingival recession has occurred and is away from the cementoenamel junction. The processor is configured to determine the pocket depth in relation to the recessed gingiva margin by determining the pocket depth in accordance with any of the embodiments in this disclosure. The determination of the loss of attachment for this embodiment is disclosed in the following paragraphs and takes into consideration both the pocket depth and gingival recession.

In an embodiment where there is a gingival recession, the insertion length still represents the periodontal pocket depth. However, the loss of attachment is equal to a combination of the insertion length and distance between the cementoenamel junction and recessed gingiva margin. The (recessed) gingiva margin is at least substantially misaligned with the cementoenamel junction and the processor is configured to determine the pocket depth in relation to the gingiva margin in accordance with one of the disclosed embodiments. Additionally or alternatively, the processor is configured to identify the cementoenamel junction and the recessed gingiva margin by applying the image processing technique (described later), and determine gingiva recession by determining a distance between the cementoenamel junction and recessed gingiva margin. The processor is further configured to calculate the loss of attachment based on the determined pocket depth and determined gingiva recession. Such calculation may include adding the determined pocket depth and determined gingiva recession. In another embodiment, the processor is configured to identify the cementoenamel junction by applying the image processing technique (described later); determine the probe tip section, visible outside the pocket, that at least substantially aligns with the identified cementoenamel junction; and determine the attachment loss based on the probe tip section aligned with the cementoenamel junction. Such determination may be performed in accordance with any of the embodiments included in this disclosure, for example by directly reading the depth from the probe tip section that aligns with the cementoenamel junction, or by using at least one of the probe profiles. Utilizing visible contrast (difference in luminance and/or color) between enamel of the crown and cementum of the root; in any of these embodiments, the processor is configured to identify the cementoenamel junction based on difference in contrast along the tooth surface. The skilled person would appreciate that gingival recession may happen at one or more discrete points and measurement of pocket depth, gingival recession and loss of attachment is therefore a function of whether there is a gingival recession at the discrete point for which the measurement is taken.

The insertion length refers to the length of the probe tip that penetrates between the tooth and gingiva until the distal point of the tip interfaces or is at least substantially close or resting close to the epithelial attachment when a predefined insertion force on the probe tip is applied. Irrespective of presence or absence of the gingival recession, the determined insertion length represents the depth of the periodontal pocket.

In different embodiments, the predefined insertion force may typically be between 20 and 25 g (i.e., 0.20-0.25 N) as this generally causes minimal discomfort and still enable accurate diagnostic readings. Other value for the predefined insertion force is within the scope of the disclosure.

According to an embodiment, a system for measuring a depth of a periodontal pocket is disclosed. The system includes a frame, at least one camera, and a processor. The frame is configured to be worn by a user. The at least one camera is attached to the frame and configured to capture at least one 2D image of an intraoral target area. The at least one 2D image includes a representation of at least a part of the tooth, a cementoenamel junction adjacent to the at least a part of the tooth, and a probe tip when the probe tip is inserted into the periodontal pocket. The processor is configured to receive the captured at least one 2D image. The processor is further configured to determine, in relation to the cementoenamel junction, at least one of gingiva recession and/or the loss of attachment by applying an image processing technique on information obtained about alignment of the probe tip with the cementoenamel junction in the captured at least one 2D image. The system disclosed in this embodiment is configured to include one or more of the embodiments that are disclosed later.

In an embodiment, the system includes the processor (such as on-board processor) that is configured to receive the at least one 2D image and determine the insertion length. Such on-board processor may be arranged on the frame itself, and/or includes a body worn processor such as a belt worn processor that is connectable to other components arranged on the frame, or a combination thereof where part processing is performed by a processor on the frame and other part of the processing is performed by the body worn processor. Additionally or alternatively, the processor includes an onboard processor and a remote processing unit. The system includes a communication module that is configured to transmit, through wired or wireless communication, the at least one 2D image and/or the real time image data to a remote processing unit, which may be considered part of the system. The remote processing unit is configured to i) receive the at least one 2D image or real time image data from which the remote processor may extract at least one 2D image, and ii) process the at least one 2D image or real time image data, for example to determine the insertion length. In an embodiment, the on-board processor may be configured to perform pre-processing on the received real time image data and using the communication module, may transmit the pre-processed image data to the remote processing unit. The remote processing unit may be configured to perform further processing on the transmitted pre-processed image data received from the communication module. Such pre-processing may include compressing the at least one 2D image and/or real time image data before transmission, resulting in optimum utilization of a communication channel. The remote processing unit may be configured to be prevented from directly controlling operation of digital dental loupe system components such as camera, light source, etc. but may include components such as analysis module for processing the data. Typically, such remote processing unit includes more processing or computing power than the on-board system processor because such further processing requires more processing than the one required for pre-processing the data. This approach allows for ensuring that the system is able to cope with large amounts of data that is captured by the at least one camera, thereby addressing systemic latency problems that may occur due to relatively limited amount of processing power of the on-board system processor. In different embodiments, the functionalities of the on-board processor and the remote processing unit may be set differently but with a consideration that majority of processing takes place at the remote processing unit.

In an embodiment, the frame may typically resemble an eyeglass frame or head mounted frame or a combination thereof. The frame may be made up of a single part or include multiple parts that are detachably connectable to one another. For example, one part is a head-mounted frame comprising the camera and light source and a second part defined by an eyeglass frame comprising a display and preferably the processor or communication module. Such a detachably connectable frame includes the possibility of connecting multiple parts mechanically and/or electrically in a detachable manner. The disclosed embodiments of the frame may be used in conjunction with one or more disclosed embodiments.

In one embodiment, the at least one camera is attached centrally to the frame. However, preferably in another embodiment, the at least one camera includes a pair of cameras individually attached proximal to opposite lateral ends of the frame in at least substantial symmetry. The term opposite lateral ends of the frame include positions that are laterally separated from each other along a horizontal axis, which may be defined by line connecting pupillary distance of the user. Thus, the pair of cameras need not be position on upper opposite lateral ends of the frame and may very well be at a distance away from the upper opposite lateral ends of the frame, i.e. towards the center of the frame. In general, the pair of cameras are at least spatially separated by a known distance. The known distance between the cameras of the pair of cameras and preferably their known imaging angle allows for capturing stereoscopic real time image data. The use of a stereoscopic real time image data enables stereopsis to be maintained, thereby allowing the user to perceive depth, enabling the periodontal probe or other dental instrument to be accurately moved in a desired direction while the user is viewing the stereoscopic real time image data. As used herein, the term "stereopsis" refers to the process in visual perception leading to the sensation of depth from viewing two optically separated projections of the intraoral target area projected onto a person's two eyes, respectively.

In an embodiment, a method for obtaining stereo alignment between the real time image data acquired by the pair of cameras is disclosed. The pair of camera includes a first camera and a second camera, arranged on the frame or a mount separate from the frame, that are spatially separated from each other. The method includes synchronizing the first camera and the second camera to individually capture real time image data at least substantially simultaneously; acquiring, at least substantially simultaneously, a first current frame (or image) using the first camera and a second current frame (or image) using the second camera, the first current frame (or image) and second current frame (or image) corresponding to individually captured real time image data respectively; identifying corresponding points between the first current frame (or image) and second current frame (or image), the corresponding points defining points that are tracked between the first current frame (or image) and second current frame (or image); and transforming the second current frame (or the first current frame) using the identified corresponding points.

In the embodiment defined in the preceding paragraph, synchronizing includes time synchronization between the first camera and the second camera such that a camera frame (or image) of a first real time image data and corresponding second camera frame (or image) of second real time image data is acquired at least substantially simultaneously by the first camera and the second camera respectively. The first camera and the second camera may preferably have same frame rate. Prior to the identification of the corresponding points, a point may be determined for the first current frame using a feature detection algorithm. Determined points are typically corners of the object in the acquired image. This may include corner of the probe, tooth, etc. It may be further determined whether the first current frame includes a minimum number of points such as at least 10, preferably at least 20. If not, then a further step of identification for the minimum number points may be performed prior to identification of the corresponding points using the feature detection algorithm such as corner detection algorithm (e.g. Shi-Tomasi corner detection algorithm or Harris corner detection). Furthermore, identification of the corresponding points may be performed by determining a point in the second current frame corresponding to the point of the first frame. This may be performed by utilizing an algorithm such as Lucas-Kanade algorithm, and particularly, sparse iterative version of the Lucas-Kanade optical flow pyramid algorithm. The Lucas-Kanade algorithm may also be based on the luminance I of RGB color model. In an embodiment, the transforming may include determining a stereo conversion formula based on a difference between the coordinates of the corresponding points, and converting the coordinates of the second current frame (or the first current frame) based on the stereo conversion formula to obtain a stereo aligned image. The stereo conversion formula may express an average conversion for all corresponding points. The conversion formula may include a matrix.

In order to avoid or at least substantially reducing the latency problem, a processer that is comprised in the i) frame, or ii) a mount that is configured to be arranged on the user of the system and in wired connection with the pair of camera and display performs the disclosed stereo alignment method. Such processor may include one of Field-Programmable Gate Array (FPGA), Digital Signal Processor, Advanced RISC Machine (ARM) processor, or a combination thereof.

The at least one camera may be arranged on the frame such that an optical axis of the at least one camera is below a reference line. The reference line may be defined by a resting part, comprised in the wearable frame, configured to rest the frame on the user. The at least one camera may be arranged on the frame such that an imaging angle between the reference line and the optical axis is defined by an angle that keeps the user's view of the display at least substantially straight in line with the reference line when the frame is worn by the user while the optical axis is directed towards the intraoral target area. Because the at least one camera is arranged to have its optical axis facing downwards, an ergonomically friendly posture for the user is achieved because the need to bend in order to capture at least one 2D image is avoided.

According to an embodiment, the imaging angle is between a range of 30 degrees to 70 degrees, such as 60 degrees. The angle may be fixed at a certain imaging value without a possibility to change the angle. Alternatively, the imaging angle may be changed and fixed at a selected value between the imaging angle range. The interface connecting the camera on the frame may include a rotation joint that is configured to rotate the camera such that the imaging angle can be changed and fixed at the selected value. The rotating joint may include specific stop positions to allow for fixing the camera at a selected imaging angle associated with a specific stop position.

In an embodiment, the frame includes a display that is arranged onto the frame using a joint around which the display can be rotated such that the display can be moved away from line of sight of the user. Similarly, the display can be rotated back in line of sight of the user. The user may thus rotate the display in and out of line of sight of the user, thus allowing the user to rotate the display out of line of sight when the user intends to communicate with the patient while the frame is still mounted onto the user.

The system may further include at least one light source that is attached to the frame and configured to illuminate the intraoral target area of a patient. In one embodiment, the at least one light source may include a pair of light sources separately attached to the opposite lateral sides of the wearable frame, such as ring LEDs around individual cameras of the at least one camera. Additionally or alternatively, the at least one light source may be attached centrally on the frame. The imaging angle of the at least one camera and illumination axis defined by the direction of the light from the at least one light source is arranged such that the light from the at least one light source is directed to the intraoral target area. Having the at least one light source integrated with the frame and arranged such that the illumination axis is correlated with the imaging angle allows for precisely illuminating the intraoral target area, thus allowing for more reliable capturing of the at least one 2D image or real time image data based on which the processing is performed.

In an embodiment, the system includes a display such as a head mounted display that is configured to display real time image data of the intraoral target area captured by the at least one camera. Providing the real time image data on the display allows for avoiding the need to look away such as to a computer screen from the patient. The display is arranged on the wearable frame such that the display is along the reference line and above the optical axis of the at least one camera. The reference line may be defined by a resting part, comprised in the wearable frame, configured to rest the frame on the user. Thus, the display is in front of the user's eye when the frame is worn by the user, typically at same level as the user's eyes along the reference line. This offers an ergonomically friendly posture for the user as the need to hunch over to look at the intraoral target area for long periods of time is avoided, thus allowing the user to concentrate on the dental procedure as the need to look at a separate screen in the user's work area is eliminated. This arrangement of the display may work particularly well ergonomically when the camera is facing downwards as discussed earlier.

In an embodiment, the system may include an additional display, such as a virtual reality display that may be worn by a person other than the user wearing the frame. The system is configured to populate the real time image data on the additional display so that the person may also follow the dental procedure and see the dental condition of the patient dentition. In situations when such person includes a clinician trainee, such virtual display may be part of the training program for the person.

In an embodiment, capturing the at least one 2D image is performed individually at one or more discrete points along the gingiva margin. Thus, at each of the discrete points one or more 2D images may be captured. Such capturing may be on at least one of the facial side and/or lingual/palatal side of the tooth. For example, examination of depth and capturing of the at least one 2D image may be performed at points selected from one or more of mesiobuccal, buccal, distobuccal, oral, mesiooral and distooral. In another embodiment, capturing includes capturing the at least one 2D image continuously along the entire gingiva margin or continuously along a section of gingiva margin on the facial side and/or lingual/palatal side of the tooth.

The system may further include a mouth mirror that is configured to provide an indirect vision, to the at least one camera, of areas at least substantially inaccessible or inconveniently accessible in the direct field of view of the at least one camera. Such areas may include the lingual/palatal side of the tooth or occasionally a few areas of the facial side such as buccal side of the tooth.

The at least one light source is configured to be oriented or the mouth mirror is positioned during use in relation to the light source such that light directed from the at least one light source on the mouth mirror illuminates areas that are at least substantially inaccessible or inconveniently accessible in the direct field of view of the camera. Such areas may include one or more of i) surfaces on the lingual or palatal side such as tooth surface, or ii) gingiva adjacent to the tooth surface and probe tip when the probe tip is inserted into the periodontal pocket on the lingual or palatal side. The at least one camera is configured to capture the at least one 2D image or real time image data of the areas that are at least substantially inaccessible or inconveniently accessible in the direct field of view of the camera, as reflected by the mouth mirror. Although the disclosure describes use of the mouth mirror in relation to the lingual/palatal side, it would be apparent to the skilled person that the mouth mirror in combination with the at least one light source and the at least one camera may be used for the buccal side of the tooth using the same principle as described for the lingual/palatal side. Using the at least one light source and at least one camera attached to the frame may be particularly helpful in capturing the at least one 2D image/real time image data from the at least substantially inaccessible or inconveniently accessible areas.

The information obtained about the probe tip in the captured at least one 2D image may include a digital representation of the probe tip visible outside the periodontal pocket. In one embodiment, the probe tip includes depth markers, which typically include either color coded marking, graduated marking or any other indicators representing length between a distal point of the probe tip and a plurality of depth markers of the probe tip. The person skilled in the art may envisage a number of different visual markings, including but not limited to, different shapes, widths, colors, etc. that provide the same function as the depth markers, i.e. an indication between the distal point of the tip to these depth markers. The information obtained about the probe tip in the captured at least one 2D image includes a digital representation of at least one depth marker comprised in the probe tip. Additionally or alternatively, the probe tip or any other probe part may include fiducial markers. The fiducial markers of at least one of pattern, size, shape, color preferably different and more preferably contrasting with colors present in the intraoral target area or any combination thereof. An image analysis of the fiducial markers, as captured in the at least one 2D image, may serve as indicative of position for insertion length determination and orientation of the probe. The fiducial markers may be same, but preferably at least some of these fiducial markers are different. Having at least some of the different fiducial markers allow for easier, quicker or more reliable identification in the at least one 2D image. The information obtained about the probe tip in the captured at least one 2D image includes a digital representation of at least one fiducial marker comprised in the probe tip or any other probe part. In an embodiment, the probe tip is devoid of any marking such as devoid of depth markers or fiducial markers, i.e. the probe does not include any indication of length from the distal point of the probe tip to a point along length of the probe tip. The information obtained about the probe tip in the captured at least one 2D image includes a geometrical information about the probe tip with or without any other part of the probe. Such geometrical information represents representation of the probe from a specific viewpoint/perspective.

In one embodiment, the intraoral target area may be provided with additional fiducial markers placed onto the patient's intraoral target area. Such placement of the additional fiducial markers may be done before and/or in a break during the capturing of the real time image data. The relative positions between the additional fiducial markers in the intraoral target area is preferably fixed during capturing the real time image data. For example, if the user is going to determine periodontal depth for a tooth of the lower jaw, then the additional fiducial markers need to be placed on the lower jaw. If the additional fiducial markers are placed onto for example the upper jaw, they have limited use only because the jaws can move relative to each other all the time. Such additional fiducial markers may be same but preferably, at least some of these additional fiducial markers are different in shape, size, color, or other properties and most preferably different from the fiducial markers, or depth indicators of the probe tip. Having different additional fiducial markers allow for easier or more reliable identification of object types in the at least one 2D image. Using such additional fiducial markers of known pattern and/or size may serve as real world anchors of location, orientation and scale.

The processor may include an analysis module that is configured to apply the image processing techniques to process the captured at least one 2D image and/or the real time image data. The image processing technique may utilize feature detection techniques that allows for detecting features of the at least one 2D image and/or real time image data from which at least one 2D image may be extracted. This may include identifying image features such as lines, edges, corners, ridges, point clouds, corners, point blobs, luminescence, color and so on. Applying image processing techniques also allows the analysis module to recognize specific object types in the image data. Thus, the analysis module may recognize one or more object types such as a tooth including tooth type such as incisors or molar, actual tooth position in mouth. i.e. tooth number according to some tooth numbering scheme, cementoenamel junction, gingiva, gingiva margin, other dentition feature, discrete point type such as mesiobuccal or oral, probe tip, depth markers, fiducial markers, additional fiducial markers, probe element, other probe parts, or other dental instruments such as mouth mirror. For example, the analysis module is configured to compare the image features from the received at least one 2D image to a reference data set, which may include a store of models or images of features relating to an object type. In some embodiments, the analysis module may extract a model, image, set of edges, a point blob, set of contours, and/or other representation of a feature from the image data. The analysis module may then compare the extracted model, set of edges, point blob, set of contours, image or other representation of the object feature to a data store of features of the stored object types. A most similar stored feature may be selected based on the comparison for example by employing a point by point comparison, edge comparison, or other comparison of the extracted feature representation to the representations of object type related features in the data store, leading to identification of the object type present in the at least one 2D image or real time image data. In one embodiment, the image processing technique utilizes machine learning techniques. The recognition of the object type includes recognizing object types based on a comparison or matching content of the at least one 2D image/real-time image data with object-type specific trained data set(s) that may have been created using machine learning techniques such as neural networks. For example, the analysis module is configured to receive the at least one 2D image, to segment the at least one 2D image into a number of segments representing object types for example by applying pixel based segmentation technique, block based segmentation technique, or any other conventionally known segmentation technique, selecting a segment from the number of segments that is associated with a plurality of distinct features; compute an aggregation of the plurality of distinct features to generate a single feature describing the object type, and recognizing a type of the object based upon the aggregation by comparing the aggregation to features corresponding with known object types from the object-type specific trained data set. The processor is configured to apply any of the image processing techniques in order to identify the probe tip section that is at least substantially aligned with the cementoenamel junction and/or with the gingiva margin.

The analysis module may also be configured to apply the image processing technique to pre-process the real time image data and/or at least a part of the at least one 2D image. This may include at least one of performing re-sampling in a new coordinate system, performing noise reduction, enhancing contrast, adjusting scale, etc. Such pre-processing may allow for providing more accurate results when the image processing techniques are applied to identify features and/or object types.

As previously discussed, in an embodiment, the analysis module of the processor is configured to apply the image processing techniques, preferably after pre-processing the image, to determine tooth type like incisor or molar, and preferably also the discrete point along the gingiva margin adjacent to the tooth type in the at least one 2D image and/or real time image data with or without determination of actual tooth position in mouth i.e. tooth number according to some tooth numbering scheme. Identification of the discrete point may be useful in creating patient dental chart where identified discrete point specific depth is entered automatically. In another embodiment, the analysis module may be configured to i) receive a real time image data, preferably after pre-processing the real time image data, representing a tooth and gingiva margin adjacent to the tooth; ii) track the probe tip, along and/or proximal to the gingiva margin, in the real time image data such as in the sequence of 2D images by applying the image processing techniques; and iii) determine a tooth type corresponding to the tooth and/or a discrete point type on the gingiva margin based on a tracking information relating to the tracked probe tip. The tracking of the probe tip in the real time image data comprises identifying the probe tip in the real time image data and identifying movement of the identified probe tip in the real time image data based on a change in position of the probe tip in the real time image data. Thus, the analysis module of the processor is configured to apply the image processing techniques, preferably after pre-processing the real time image data, to determine tooth type, and preferably also the discrete point along the gingiva margin adjacent to the tooth type in the at least one 2D image based on the tracked probe tip with or without determination of actual tooth position in mouth. I.e. tooth number according to some tooth numbering scheme. Using historical data of the movement of the probe tip as a reference data in relation to movement along different dental objects in the intraoral area allows for improving the accuracy of determining the tooth type and/or the discrete point where the depth measurement is made because the processor may take into account additional information comprising the path that the probe tip followed to reach the current tooth and discrete point.

The analysis module of the processor may be configured to apply the image processing techniques, preferably after pre-processing the image, to recognize object type such as gingiva margin, cementoenamel junction and probe tip in the at least one 2D image. In an embodiment, the analysis module is configured to apply the image processing techniques to identify, from the digital representation of the at least one depth marker that is aligned or closest to the representation of the gingiva margin and/or cementoenamel junction in the at least one 2D image. Additionally or alternatively, the analysis module is configured to apply the image processing techniques to identify, from the digital representation of the fiducial markers visible outside the gingiva margin in the at least one 2D image, such fiducial markers being present on the probe. Additionally or alternatively, the analysis module is configured to apply the image processing techniques to identify, from the digital representation of the geometry of at least the probe tip, preferably of the probe, visible outside the gingiva margin in the at least one 2D image.

In an embodiment, the processor may further be configured to read the periodontal pocket depth measurement directly from the identified depth marker that is aligned or closest to the representation of the gingiva margin in the at least one 2D image. Additionally or alternatively, the processor may further be configured to read the loss of attachment directly from the identified depth marker that is aligned or closest to the representation of the cementoenamel junction. Additionally or alternatively, the processor may further be configured to read the gingiva recession directly from a first identified depth marker that is aligned or closest to the representation of the cementoenamel junction and a second identified depth marker that is aligned or closest to the recessed gingiva, the difference between the first identified depth marker and the second identified depth marker representing the gingiva recession. This approach may be useful when the probe tip includes specific measurements such as in mm from the distal tip of the probe tip.

Additionally or alternatively, the processor is configured to correlate the identified depth marker that is aligned or closest to the representation of the gingiva margin and/or cementoenamel junction in the at least one 2D image with a probe profile. The probe profile includes a digital specification such as geometrical information about the probe tip or parts (depth markers) thereof, indicating the length between the distal point of the probe tip and a plurality of depth markers of the probe tip. The correlation between the identified depth marker and the digital specification allows for identifying a measurement from the digital specification that corresponds to the identified depth marker. This allows for determining at least one of the i) periodontal pocket depth based on the identified depth marker that is at least substantially aligned with the gingiva margin, ii) for gingival recession scenario, loss of attachment based on the identified depth marker that is at least substantially aligned with the cementoenamel junction, or iii) gingival recession based on a first identified depth marker that at least substantially aligns with the cementoenamel junction and a second identified depth marker that at least substantially aligns with the recessed gingiva margin.

Additionally or alternatively, the processor is configured to correlate the identified fiducial markers visible outside the periodontal pocket with a probe profile. Such correlation may be in relation to one of the gingiva margin, recessed gingiva margin or cementoenamel junction. The probe profile includes digital specification, such as geometrical information about the fiducial markers, having an interpretation of fiducial markers indicating the length between the distal point of the probe tip and fiducial markers of the probe tip and/or distance between different sections of fiducial markers. This allows for determining the periodontal pocket depth and/or gingival recession and/or loss of attachment.

Such digital specification may also include interpretation of fiducial markers such that orientation of the probe in relation to the tooth and/or any other intraoral cavity organ may be determined. The correlation between the identified fiducial markers and the digital specification allows for identifying a measurement depth from the digital specification corresponding to the identified fiducial marker, thus allowing for determining at least one of the i) periodontal pocket depth based on the identified fiducial markers, ii) loss of attachment based on the identified fiducial marker in relation to the identified cementoenamel junction, iii) gingival recession based on the fiducial marker in relation to the identified cementoenamel junction and recessed gingiva margin. The analysis module may further be configured to determine correlation of the identified fiducial marker with the digital probe profile in order to determine orientation of the probe because the fiducial marker is represented uniquely when the probe is in a certain orientation. The probe profile may also include a distinct fiducial marker(s), specific to a discrete point, that represents optimum orientation for performing depth measurement for the specific discrete point. The processor may be configured to determine whether orientation of the probe is optimum for pocket depth measurement by comparing the identified fiducial marker with the distinct fiducial marker(s). The term optimum relates to a specific orientation of the probe that is predetermined and stored in a memory to be acceptable for recording the insertion length. Such specific orientation may be specific to different discrete measurement points. If not, then the processor may be further configured to instruct a notification module to notify the user of the discrepancy for example the processor may notify the user for example through an audio message stating "change the orientation and take a new measurement". The system may include a speaker module to deliver such audio messages. The user may change the orientation of the probe for taking another measurement. The processor is configured to determine whether the orientation of the probe is optimum before the image processing technique is applied for determining the pocket depth. This approach may be particularly useful in ensuring that the measurements are reliable and independent of the user's skill set. In an example, the processor is configured to, using the image processing techniques, determine whether for a specific discrete measurement point, the probe tip is parallel to the long axis of the tooth. The processor may be configured to instruct a notification module to notify the user of discrepancy when such determination is negative, i.e. the orientation of the probe while taking the measurement is not optimum, and the user may take another measurement for the specific discrete point.

In an embodiment, the processor is configured to correlate a visible part of the probe tip with a probe profile. The visible part, as represented in the at least one 2D image, includes a part of the probe tip visible outside the periodontal pocket or a part of the probe tip visible from the cementoenamel junction in a direction away from the gingiva. The probe tip typically is devoid of any depth related marking or fiducials. The probe profile includes digital specification such as geometrical information about the probe including different projected views of the probe when viewed from different perspectives. The digital specification may further include length information about distance between a certain point on the projected view and distal point of the probe tip in the projected view. Such correlation includes comparing, such as by superimposing, the visible part of the probe with different projected views, and identifying a projected view that matches at least the visible part, wherein a non-overlapping section between the visible part comprising the part of the probe tip visible outside the periodontal pocket and the matched projected view represents the pocket depth. The processor is configured to determine the pocket depth from the digital probe profile based on the length information about the non-overlapping section. Additionally or alternatively, the correlation includes comparing, such as by superimposing, the visible part of the probe with different projected views, and identifying a projected view that matches at least the visible part, wherein a non-overlapping section between the visible part comprising the part of the probe tip visible from the cementoenamel junction in a direction away from the gingiva and the matched projected view represents the loss of attachment. The processor is configured to determine the loss of attachment from the digital probe profile based on the length information about the non-overlapping section. In another embodiment, the processor is configured to determine the gingival recession based on the difference between the determined length of the periodontal pocket and the determined length of the loss of attachment. Additionally or alternatively, the processor is configured to determine the orientation of the probe based on the matched projected view. In addition, the probe profile may also include a distinct projected view, specific to a discrete point, that represents optimum orientation for performing depth measurement for the specific discrete point. The processor may be configured to determine whether orientation of the probe is optimum for pocket depth measurement by comparing the identified perspective with the distinct projected view. If not, then the processor may be further configured to instruct a notification module to notify the user of the discrepancy. For example, the processor may notify the user through an audio message stating "change the orientation and take a new measurement". The system may include a speaker module to deliver such audio messages. The user may change the orientation for taking another measurement. The processor is configured to determine whether the orientation of the probe is optimum before the image processing technique is applied for determining the insertion length. This approach may be particularly useful in ensuring that the measurements are reliable and independent of user's skill set. In an example, the processor is configured to, using the image processing techniques, determines whether for a specific discrete measurement point, the probe tip is parallel to the long axis of the tooth. The processor may be configured to instruct a notification module to notify the user of discrepancy when such determination is negative, i.e. the orientation of the probe while taking the measurement is not optimum, and the user may take another measurement for the specific discrete point.

Although the embodiments above may employ different techniques to determine the pocket depth, the skilled person would appreciate that the means of determining orientation such as using fiducial markers and/or projected views may be used in any of the embodiments disclosing determination of the pocket depth. For example, projected view approach for determining orientation may be used where the pocket depth is determined using depth markers. Similarly, fiducial marker approach for determining orientation may also be used where the pocket depth is determined using projected view. The skilled person would readily observe that in order to utilize different approaches simultaneously, both the probe that is used for depth measurement and the probe profile need to be modified in accordance with the above disclosure. For example, fiducial marker approach for determining orientation may be used where the pocket depth is determined using projected view would require the probe to include fiducial markers and probe profile to include interpretation of such fiducial markers. Such combined approach may increase the accuracy of determination of the pocket depth, gingival recession and loss of attachment.

In an embodiment, the processor is further configured to record the at least one 2D image that is used to determine the periodontal pocket depth. The recorded image may be stored in a database. Additionally, the processor may be configured to associate the recorded image with the patient record such as a dental chart. The processor may further be configured to generate a patient record that may be visually presented on the display comprised in the system or any other remote display, the patient record may include an access like a link to the recorded at least one 2D image. The processor may be configured to access the recorded at least one 2D image and render the accessed recorded at least one 2D image on the display or any other remote display.

In an embodiment, the processor is configured to identify the tooth type corresponding to the tooth and/or discrete point type represented in the at least one 2D image with or without identification of actual tooth position in mouth i.e. tooth number according to some tooth numbering scheme. This may be achieved by receiving a user instruction for manual indication of the tooth type and/or discrete point type represented in the at least one 2D image. As the user can manually identify the tooth such as tooth type and/or discrete point type, the user may simply provide instructions for example by way of a voice command indicating the tooth for which the measurements are taken. The system may include a microphone that is configured to receive the voice commands from the user and the processor is configured to convert the received voice command into an instruction, representative of the voice command, that allow for storing the received voice command in the patient record. The microphone is preferably mounted on the wearable frame and has microphone directionality directed towards the user's mouth. Additionally or alternatively, the system may include other input means such as a user interface by way of touchscreen or physical buttons to enter the tooth type and/or discrete point type information.

In an embodiment, tooth and/or discrete point type represented on the at least one 2D image or in real time image data may be identified automatically. Such automatic identification may utilize the image processing techniques described earlier. For example, the automatic identification may utilize machine learning techniques using convolution neural network. By way of example an automatic identification technique may include providing the at least one 2D image, generating data for identifying the object by extracting a feature vector from at least a partial area of the captured image data, and identifying a class to which the object belongs based on the data for identifying the object and an object dictionary data generated from previously recorded image data or a trained data set. The feature vector may include multiple elements (features). The features may represent a pixel or a whole object in the at least one 2D image. Examples of features are color components, length, area, circularity, gradient magnitude, gradient direction, or simply the gray-level intensity value.

The determination of the periodontal pocket depth and automatic identification of the tooth type and/or discrete point type may allow for automatically recording the determined periodontal pocket depth. In an embodiment, the processor is configured to generate instructions for automatically recording the pocket depth for the identified tooth in a digital patient record such as in a dental chart. The digital patient chart may be stored in a database. Furthermore, applying the image processing techniques (disclosed earlier) on the captured at least one 2D image, the analysis module may be configured to identify discrete points at which the periodontal pocket depth is determined. Thus, the determined periodontal pocket depth for one or more discrete points for the identified tooth may be stored visually on the dental chart where for determined pocket depth corresponding to one or more discrete points for the identified tooth is represented. The diagrammatic representation of teeth along with periodontal pocket depth is particularly useful for the user for monitoring and diagnostic purposes.

In an embodiment, the processor is configured to create a depth profile for the tooth based on the determined pocket depth. The depth profile includes a collection of pocket depths at one or more points along the gingiva margin or along the entire length of the gingiva margin or a portion of the gingiva margin on the facial side and/or lingual/palatal side of the tooth. In case the determination of the pocket depth is at one or more discrete points, the depth profile includes collection of pocket depths for some or all of these discrete points. In another embodiment where the determination of the pocket depth is for the entire gingiva margin or a portion of the gingiva margin, then the depth includes collection of all points that are continuously on the entire of the gingiva margin or portion of the gingiva margin respectively. The depth profile may be recorded as information data represented at least one of preferably on the patient record such as on a patient's dental chart, or in a tabular form for one or more patient's teeth, or any other intuitive layout.

In an embodiment, the processor is configured to create a first depth profile and time-stamp the first depth profile with a first-time stamp to create a time stamped first depth profile. The processor is configured to create a second depth profile and time-stamp the second depth profile with a second-time stamp to create a time stamped second depth profile, the second time-stamp being different from the first time-stamp. These time stamps, typically expressed as a sequence of digitally encoded information, identify when the first depth profile based on depth measurements at first time and second depth profile based on depth measurement at second time were created. The time stamps may include specific dates (or even specific hour or minutes of the date) when individual depth measurements corresponding to the first depth profile and second depth profile were made. The processor is further configured to calculate a difference between the first depth profile and the second depth profile, i.e. calculated depth difference. The difference between the first depth profile and the second depth profile is calculated for the same tooth. Furthermore, the difference is typically calculated for corresponding points in the first depth profile and the second depth profile. For example, a difference is calculated for a tooth between a first depth measurement from the first depth profile for mesiobuccal and a second depth measurement from the second depth profile for mesiobuccal. Similarly, the difference may be calculated for one or more of buccal, distobuccal, oral, mesiooral, etc.

In an embodiment, the processor is configured to calculate a time difference between the first time-stamp and second time-stamp, i.e. calculated time difference; and calculate a rate of change, i.e. calculated rate change, of the pocket depth based on the calculated difference and calculated time difference.

In an embodiment, the processor is configured to identify a development of a dental condition based on at least one of the depth profiles, the calculated depth difference or the calculate rate difference. The user may predefine dental condition as represented by a dental health classification, typically based on clinical rules, such as severe, moderate, mild or healthy for at least one of different depths, different difference ranges or range of rate of change. Additionally or alternatively, such dental health classification may by defined, typically based on clinical rules, in the system as part of factory setting and/or any other person such as clinician who may not be the user of the system. For example, determined depth a (like less than 3 mm) is classified as healthy, b is classified as mild, c is classified as moderate, and d is classified as severe where absolute values d>c>b>a. Another example relating to the depth difference, a depth difference from 0 to less than DIFF1 is classified as healthy, from DIFF1 to less than DIFF2 is classified as mild, from DIFF2 to less than DIFF3 is classified as moderate, and from DIFF3 or more is classified as severe, where absolute values DIFF3>DIFF2>DIFF1>0. Similarly, the user may define range for rate of change to classify the rate of change as healthy, mild, moderate or severe. It would be apparent to the skilled person that other classifications based on the depth profile, difference or rate of change ranges may also be considered.

In an embodiment, the processor is configured to compare the at least one of depth profile, calculated depth difference or calculate rate change with the user defined classification and determine a dental health classification of a user's dental condition. In another embodiment, the processor is configured to compare only one of the depth profile, calculated depth difference and calculated rate change against respective classification and determine a dental health classification. In another embodiment, the processor is configured to compare at least two of the depth profile, calculated depth difference and calculate rate change against respective classifications and determine a dental health classification of user's dental condition only if both the classifications are matching. For example, the dental health condition is classified as mild when individual comparison of the depth difference against respective classifications determines the dental health condition is classified as mild and comparison of the calculated rate change against respective classifications is also classified as mild. In yet another embodiment, the processor is configured to compare at least two of the calculated depth difference and calculated rate change against respective classifications and determine a dental health classification of user's dental condition based on worse of the two classifications. For example, the dental health condition is classified as severe when individual comparison of the calculated depth difference against respective classifications determines the dental health condition is classified as moderate but comparison of the rate of change against respective classifications is classified as severe. In yet another embodiment, the processor is configured to compare all the depth profile, calculated depth difference and calculated rate change against respective classifications and determine a dental health classification of user's dental condition only if at least two of the classifications are matching. For example, if the comparison of depth profile with respective classification determines a healthy condition, comparison of the calculated depth difference with the respective classification determines a mild condition and comparison of the calculated rate change with respective classification determines a mild condition, then the dental health condition is classified as mild. In yet another embodiment, the processor is configured to compare all the depth profile, calculated difference and rate of change against respective classifications and determine a dental health classification of user's dental condition in accordance with the worst of classification. For example, if the comparison of depth profile with respective classification determines a moderate condition, comparison of the calculated depth difference with the respective classification determines a moderate condition and comparison of the calculated rate change with respective classification determines a severe condition, then the dental health condition is classified as severe. In any of the preceding embodiments, the respective classifications are stored in a memory and the processor is configured to access at least one the classifications from the memory and compare at least one of the depth profile, depth difference or rate change with the accessed one of the classifications that corresponds to respective depth profile, depth difference or rate change. In any of the preceding embodiments, the memory further stores the correlation of these classifications with possible dental conditions including possible dental diseases. The processor is configured to match the determined classification with one or more possible dental conditions including possible dental diseases.

As the rate of change of the periodontal pocket depth indicates how fast the pocket depth is increasing, in an embodiment, the processor is configured to predict a future pocket depth in accordance with the determined rate of change and a specified time.

$$R=\Delta D \Delta R=(|D1-D1|)/(|(T2-T1|)$$

$$FD=D2+(|FT-T2|*R)$$

where, R=Rate of Change, D2=pocket depth determined at second time T2, D1=pocket depth determined at first time T1, ΔD=Difference between the second pocket depth D2 and first pocket depth D1, ΔT=Difference between the second time T2 and first time T1, FD=predicted future pocket depth at a future time FT In a different embodiment, the processor based on pocket depth measurements at different time points, is configured to determine whether the pocket depth is increasing at a non-linear rate and determine a mathematical function defining the non-linear rate of change. The processor is configured to determine a predicted future pocket depth based on the non-linear rate of change of the pocket depth. Determining the non-linear rate is useful in determining worsening of the loss of attachment.

In another embodiment, the processor is configured to measure pocket depths at different discrete points for a tooth, determine an average or weighted average of the measured pocket depths for different discrete points, where weighted average is in accordance with giving same or different weights to pocket depths corresponding to each discrete point. The processor, based on the average or weighted average for the whole tooth, is configured to generate a tooth index representing an indication of the condition of the tooth. Furthermore, applying previously recited techniques to predict future pocket depth in combination with the average or weighted average would allow for predicting future tooth index representing a future condition for the whole tooth.

Similarly, in another embodiment, the processor is configured to predict a time or time interval when the predicted pocket depth reaches a predefined threshold value.

$$R=\Delta D/\Delta T=(|D2-D1|)/(|(T2-T1|)$$

$$t=(|T-D2|)/R$$

$$Tf=|T2+t|$$

where, R=Rate of Change, D2=pocket depth determined at second time T2, D1=pocket depth determined at first time T1, ΔD=Difference between the second pocket depth D2 and first pocket depth D1, ΔT=Difference between the second time T2 and first time T1, t=predicted time interval from the second time T2 when the pocket depth would reach threshold value T, i.e. Tf defines a time point in future when the pocket depth would reach the threshold value.

Utilizing the predicted time, the processor is configured to automatically schedule an appointment for the user. In other words, the follow up appointment for the user is a date that would be defined by T2+t. It may happen that such automatic scheduling may have conflicts. The conflicts for the appointment may include at least one of a prior booked meeting, unavailability of the user such as operating clinician (user), non-working hours of the clinic. Therefore, in one embodiment, the processor is configured to access a scheduling calendar and adjust the appointment by adding an additional time (AAT), i.e. T2+t+AAT to schedule an appointment that is prevented from having the conflict. In another embodiment, the processor is configured to access a scheduling calendar and adjust the appointment by subtracting an additional time (DAT), i.e. T2+t−DAT to schedule an appointment that is prevented from having the conflict. Based on identification of the available schedule of the clinician, the processor may be configured to communicate the scheduled appointment with the patient, for example by automatically sending an email with scheduling details.

In an embodiment, the system further includes the display. The at least one camera is configured to capture real-time image data of the intraoral target area. The processor is configured to receive a virtual content such as a three-dimensional digital representation of at least the tooth with or without the cementoenamel junction and gingiva margin and overlaying the virtual content such as the three-dimensional digital representation over the real time image data such that at least a portion of the real time image data is viewable, through the overlaid three-dimensional digital representation, on the display unit in real time. The processor may be configured to capture the at least one 2D image from the captured real-time image data. Capturing the real time image data allows the user to view the intraoral target area in real time and having an overlaid virtual content allows for easily establishing a correspondence between the real time image data, i.e. the physical world and any digital information that may relate to the patient. The additional digital information for example historical dental condition data of the user may be extremely useful during a dental procedure like in measuring periodontal pocket depth.

The system thus may allow for a view of a physical, real-world environment and augments the view by the virtual content that may include graphical information, for example numerical data, non-numerical data, two dimensional images or three-dimensional models, or a combination thereof. The display may include at least one of glasses, other lenses, or a projector that projects the virtual content onto the glasses or lenses to provide a visual overlay to a dental practitioner. The visual overlay is superimposed over the real time image data that the at least one camera captures. Such display may include Augmented/Virtual Reality (AR/VR) glasses, AR/VR goggles, an AR/VR headset or other types of display of known AR or VR systems.

In an embodiment, the processor includes a registration module that is configured to overlay the virtual content over the real time image data. In an embodiment, the overlaying includes positioning a non-structural virtual content on a section of the display such that the non-structural virtual content is positioned to avoid an overlap or interference with at least a part of the representation, on the display, of the intraoral target area where a dental procedure such as periodontal pocket measurement is performed. The processor may be configured to position the non-structural virtual content at a specific pre-assigned section of the display or the processor is configured to i) evaluate the real time image data by applying the image processing technique to determine a section on the display where dental instruments such as periodontal probe relating to the dental procedure are not present and ii) displays the non-structural virtual content at the determined section. The non-structural virtual content may include patient details or other textual or pictorial record(s) like name, age, synopsis from earlier dental visits, or notes about specific dental or other health conditions and may preferably exclude a three-dimensional representation of the intraoral target area, available from a prior scan. As an example, the at least a part of the representation may include at least a representation of the gingiva margin and/or cementoenamel junction that is proximal to the discrete point where pocket depth measurement is in progress. Additionally or alternatively, the non-structural virtual content may include a menu having options that are configured to be controlled by the user preferably using voice commands. Such control of menu options using voice commands allows the user to continue focusing on the dental procedure while allowing selection of a menu option. The menu option may include controls relating to rendering patient's data and/or structural virtual content. The menu option may include control that allows the user to include voice notes to the at least one 2D image. Additionally or alternatively, the overlaying includes performing image registration between the real time image data and the virtual content such as three dimensional digital representation of the patient's oral cavity such as of the tooth and gingiva margin and/or cementoenamel junction, or other intraoral regions. The three dimensional digital representation of the patient's oral cavity may include one or more of surficial three dimensional data such as obtained from an intraoral scanner, and/or sub-surficial three dimensional data such as obtained from a cone beam computed tomography (CBCT) scanner. The registration module is configured to carry out (apply) image registration algorithms to register the real time image data from at least one camera and the virtual content such as three dimensional data relating to the intraoral cavity of the patient to each other. Such image registration may be based on marker based tracking such as using fiducial markers, markerless tracking such as feature based tracking, edge based tracking, keypoint based tracking, intensity based tracking or a combination thereof. The image registration involves determination of the transformations which spatially aligns one image with the other, i.e. virtual content with the real time image data. Image registration may involve identifying multiple points, point clouds, edges, corners, etc. in each image of an image pair, surface fitting to the points of each image, and using local searches around points to match points of the two images. For example, the registration module may be configured to match points of one image with the closest points interpolated on the surface of the other image, and iteratively minimize the distance between matched points. The registration module may be further configured to find the best match of curvature features at points of one image with curvature features at points interpolated on the surface of the other image, with or without iteration. The registration module may be also configured to find the match such as best match of spin-image point features at points of one image with spin-image point features at points interpolated on the surface of the other image, with or without iteration. Other techniques that may be used for image registration include those based on determining point-to-point correspondences using other features and minimization of point-to-surface distances. The registration module may be configured to apply other image registration techniques such as pixel wise closed loop registration approach that may automatically minimize registration errors using a reference model comprised of the real scene model and the desired virtual augmentations. Registration errors may be minimized in global world space via camera pose refinement, and local screen space via pixelwise adjustments. The registration module may be configured to apply any other conventionally known registration techniques to register the virtual content with the real time image data.

The registration module may further be configured to apply conventionally known age registration techniques to achieve temporal registration between the virtual content and real time image data. Such temporal registration would allow for synchronized motion between the received real time image data and the virtual content. In other words, the registration module is configured to update and redisplay the virtual content at least substantially at the same time corresponding to the update and changes in the real time image data. Such temporal registration techniques may also be applied in order to at least substantially address latency problems, which may include at least one of an off-host delay i.e. delay between a change and sensing the change by the system, computational delay i.e. delay caused by performing computations, rendering delay i.e. time required to render the real time image data, display delay i.e. time between creating the rendered real time image data and displaying the image, synchronization delay i.e. time waiting for other crucial data paths to catch up and frame rate delay i.e. time between the current image frame and subsequent image frame. A relative latency comprising any combination of off-host delay, computational delay, synchronization delay and rendering delay may occur. The registration module may be configured to address the relative latency in incoming real time image data by using time stamping and predictive filtering to temporally align image the data input stream.

Once the virtual content has been registered to the real time image data and transformed to match the real time image data as closely as possible, the registration modul is configured to transform the virtual content (or a portion thereof) to generate visual overlay, such transformation may be part of the registration process or a separate step. Accordingly, a patient's historical dentition or patient's intraoral target area as represented in the virtual content such as three-dimensional digital representation may be adjusted to the real time image data, and the visual overlay showing the patient's virtual content may be superimposed over the real time image data that is displayed on the display while ensuring that at least a portion of the real time image data is viewable, through the superimposed three-dimensional digital representation, on the display unit in real time.

Thus, the registration module using the image registration techniques may be configured to track the a spatial and/or temporal change between the virtual content and the real time image data and automatically maintain registration between the virtual content and the real time image data. Thus, the registration between the virtual content and the real time image data is at least substantially maintained even when the field of view of the at least one camera changes because of movement of the user and/or movement of the patient. Such tracking may employ conventionally known digital processing techniques such as comparison of image frames and/or include a separate sensor that is configured to track the movement between the real time image and virtual content and provide a tracking signal to the registration module, which may then apply registration techniques to maintain the registration.

In an embodiment, the registration module may further to be configured to automatically align the at least one 2D image, received from the at least one camera, with a three-dimensional representation of the teeth using known co-registration technique. This three-dimensional to two-dimensional image registration allows for simultaneous visualization of information contained in the at least one 2D image and the three-dimensional representation. This may be useful in many scenarios for example in guided dental operations. Co-registration techniques are generally known, for example in Mitrović, Uroš et al., "Simultaneous 3D-2D image registration and C-arm calibration: Application to endovascular image-guided interventions" Med Phys. 2015 November; 42(11):6433-47.

In an embodiment, the processor is configured to generate a measurement guideline, as part of the overlaid virtual content, corresponding to at least one of the discrete points. For example, the measurement guidelines for a specific discrete point and specific tooth are stored in a memory and the processor is configured to receive such stored guidelines and superimpose, for the specific discrete point for the specific tooth, guidelines on the three-dimensional digital representation. Because the measurement guideline provides an indication of how the probe tip needs to be angled/oriented in order to make an accurate depth measurement, the measurement guideline may be considered as an overlaid virtual indicator for performing a guided measurement of pocket depth. The processor may further be configured to receive/access or generate the measurement guidelines and overlay the measurement guideline, usually as part of the three dimensional data, over the real time image data such that at least a portion of the real time image data is viewable, through the overlaid measurement guideline, on the display unit in real time. For example, for a specific discrete point the measurement guideline may include a line that is parallel to the long axis of the tooth. The overlaid measurement guideline may include at least one of an overlaid guideline such as a line(s) indicating a direction of insertion of the probe tip, permanent colored zones (red representing wrong insertion, green representing correct insertion, and orange representing a transition between wrong and correct insertion) or a temporary overlaid guideline such as temporary colored zones (red representing wrong insertion, green representing correct insertion, and orange representing a transition between wrong and correct insertion) that appear dynamically on the basis of probe orientation as the probe tip is inserted into the pocket. Because the processor is configured to identify object types such as the probe tip, the processor is configured to track the periodontal probe utilizing the image processing techniques and determine, based on the measurement guidelines, whether the probe tip is angled/oriented correctly for a reliable measurement. As the processor is configured to recognize the tooth type and the discrete point in relation to the gingiva margin and tooth type, the processor may be configured to generate the measurement guidelines using clinical rules. Alternatively, the processor is configured to access measurement guidelines from a database that stores, usually clinically complying, measurement guidelines for specific points along the gingiva margin for a specific tooth type.

In an embodiment, the processor includes a magnification module that is configured to apply a desired digital magnification and/or optical magnification to the real time image data or to the at least one 2D image captured by the at least one camera. Such digital magnification and/or optical magnification may be set prior to or during capturing the real time image data and/or at least one 2D image and accordingly a magnified real time image data and/or magnified at least one 2D image is captured. Additionally or alternatively, the digital magnification may be applied after the real time image data and/or at least one 2D image is captured. With higher resolution, the digital magnification may be applied without substantially reducing the image quality. Thus, magnification module using a digital magnification algorithm alone may be used to provide a desired magnification level of the real-time image data/at least one 2D image. In the embodiment where optical magnification is applied, the magnification module is configured to instruct the at least one camera to adjust the lens system of the at least one camera for changing the optical magnification. Using the optical magnification alone may provide higher image quality when magnification is applied but such implementation may require additional optical components, making the frame or the mount on which the at least one camera is arranged heavy. Alternatively, using the digital magnification alone may provide lighter frame weight or weight of the mount on which the at least one camera is arranged but may compromise with image quality when magnification is applied. In an embodiment, a balance may be achieved between weight and image quality by having a magnification that is a combination of optical and digital magnification. For example, the optical magnification may be around 1.5 times and the digital magnification may be around 5 times. This allows for achieving enough magnification without adding substantial weight to the frame by way of additional optical components that are used for optical magnification. In different embodiments, the magnification may be applied globally to the whole image or locally to a specific region of interest like probe, etc.

In an embodiment, a digital loupe system is disclosed. The system includes a frame configured to be worn by a user; at least one light source attached to the frame and configured to illuminate a target area of an intrabody cavity of a patient; at least one camera attached to the frame, the at least one camera being configured to capture real time image data of the target area; a processor configured to receive the captured real time image data of the target area and generate modified image data by digitally applying a magnification factor on a region of interest within the captured real time image data; and a communication module configured to transmit the generated modified image data to a display module that is configured to display the generated modified image frames to the user.

The processor may further include a stabilization module that is configured to apply digital stabilization to compensate for blur during/in the captured at least one 2D image and/or real time image data, for example blur introduced due to user's head movements and/or patient's jaw movement. The implementation of digital image stabilization in order to counteract the blur is particularly useful when high magnification is used, whereby smallest head movements translate to a large perceived image shift, rendering the intraoral target area difficult to observe and to process the captured at least one 2D image or real time image data. The digital stabilization may be applied by using conventionally known techniques. The stabilization module may be configured to determine and apply an amount of the stabilization as a function of a magnification setting used for applying the desired digital magnification. For example, for a magnification factor higher than a predefined level, a higher stabilization is applied compared to stabilization applied for a magnification factor equal to lower than the predefined level. In one embodiment, the stabilization module is configured to determine coordinates of the object such as at least one of probe tip or tooth or gingiva margin in the acquired at least one 2D image and apply known stabilization techniques for fine stabilization of images based on a previous at least one 2D image so as to compensate for the blur. In another embodiment, the system includes a motion sensor that is configured to measure motion such as acceleration data of the user's head and further configured to generate a motion signal. The image stabilization module is configured to apply a digital stabilization as a function of the measured motion, as expressed by the motion signal.

In an embodiment, a method for digital stabilization between a first frame and a second frame of a real time image data is disclosed. The method includes acquiring, using the at least one camera, a first frame (or image) of the real time image data; acquiring, using the at least one camera, a second frame (or image) of the real time image data, the second frame (or image) being acquired at a later time than the first frame (or image); identifying corresponding feature points between the first frame (or image) and second frame (or image), the corresponding feature points defining points that are tracked between the first frame (or image) and second frame (or image); and transforming the second frame (or image) using the identified corresponding feature points.

In the embodiment described in the preceding paragraph, the later time is sequentially consecutive. In other words, the second frame is captured right after the first frame for example the latency between the frames is 50 ms or less. Also, prior to the identification of the corresponding feature points, a feature point may be determined for the first frame using a feature detection algorithm. Determined feature points are typically corners of the object in the acquired image. This may include corner of the probe, tooth, etc. It may be further determined whether the first frame includes a minimum number of features points such as at least 10, preferably at least 20. If not, then a further step of identification for the minimum number feature points may be performed prior to the identification of the corresponding feature points using the feature detection algorithm such as corner detection algorithm (e.g. Shi-Tomasi corner detection algorithm or Harris corner detection). Furthermore, identification of the corresponding feature points may be performed by determining a feature point in the second frame corresponding to the feature point of the first frame. This may be performed by utilizing algorithm such as Lucas-Kanade algorithm, and particularly, sparse iterative version of the Lucas-Kanade optical flow pyramid algorithm. The Lucas-Kanade algorithm may also be based on the luminance I of RGB color model. In an embodiment, the transforming may include determining a stabilization conversion formula based on a difference between the coordinates of the corresponding feature points, and converting the coordinates of the second frame based on the stabilization conversion formula to obtain a converted image, thus leading to stabilization between the second frame and first frame. The stabilization conversion formula may express an average conversion for all corresponding feature points. The conversion formula may include a matrix. In order to avoid or at least substantially reducing the latency problem, a processer that is comprised in the i) frame, or ii) a mount that is configured to be arranged on the user of the system and in wired connection with the at least one camera and display performs the disclosed digital stabilization method. Such processor may include one of Field-Programmable Gate Array (FPGA), Digital Signal Processor, Advanced RISC Machine (ARM) processor, or a combination thereof.

Additionally or alternatively to the digital stabilization, the system includes mechanical stabilizers, which are configured to apply mechanical stabilization to compensate for blur during the capturing of the at least one 2D image and/or real time image data, for example blur introduced due to user's head movements and/or patient's jaw movement. Using the mechanical stabilizers in order to counteract the blur is particularly useful when high magnification is used, whereby smallest head movements translate to a large perceived image shift, rendering the intraoral target area difficult to observe and to process the captured at least one 2D image or real time image data. Typically, such stabilizers may be part of the at least one camera. The mechanical stabilizers may include conventionally known devices such as gimbal for example multi-axis gimbal set.

The implementation described earlier individually with respect to stereo alignment and stabilization may be combined in order to obtain a stabilized and stereo aligned real time image data. Thus, in an embodiment, a method for digitally stabilizing images and stereo aligning images obtained from a pair of cameras is disclosed. The pair of camera includes a first camera and a second camera, arranged on the frame or a mount separate from the frame, that are spatially separated from each other. The method includes synchronizing the first camera and the second camera to individually capture real time image data at least substantially simultaneously; acquiring, at least substantially simultaneously, a first current frame (or image) using the first camera and a second current frame (or image) using the second camera, the first current frame (or image) and second current frame (or image) corresponding to individually captured real time image data respectively; obtaining a first previous frame (or image) from a memory, wherein the first current frame is acquired a later time than the first previous frame that is comprised in the real time image data acquired by the first camera; identifying corresponding feature points between the first current frame (or image) and first previous frame (or image), the corresponding feature points defining points that are tracked between the first current frame (or image) and first previous frame (or image); transforming the first current frame using the identified corresponding feature points to obtain a converted image; identifying corresponding points between the converted image and second current frame, the corresponding points defining points that are tracked between the converted image and second current frame; and transforming the second current frame using the identified corresponding points.

In the embodiment defined in the preceding paragraph, synchronizing includes time synchronization between the first camera and the second camera such that a camera frame (or image) of a first real time image data and corresponding second camera frame (or image) of second real time image data is acquired at least substantially simultaneously by the first camera and the second camera respectively. The first camera and the second camera may preferably have same frame rate. The later time is sequentially consecutive. In other words, the first current frame is captured right after the first previous frame for example the latency between the frames is 50 ms or less. The corresponding points or corresponding feature points may be at least partly same.

Prior to the identification of the corresponding feature points, a feature point may be determined for the first previous frame using a feature detection algorithm. Determined feature points are typically corners of the object in the acquired image. This may include corner of the probe, tooth, etc. It may be further determined whether the first previous frame includes a minimum number of features points such as at least 10, preferably at least 20. If not, then a further step of identification for the minimum number feature points may be performed prior to the identification of the corresponding feature points using the feature detection algorithm such as corner detection algorithm (e.g. Shi-Tomasi corner detection algorithm or Harris corner detection). Furthermore, identification of the corresponding feature points may be performed by determining a feature point in the first current frame corresponding to the feature point of the first previous frame. This may be performed by utilizing algorithm such as Lucas-Kanade algorithm, and particularly, sparse iterative version of the Lucas-Kanade optical flow pyramid algorithm. The Lucas-Kanade algorithm may also be based on the luminance I of RGB color model. In an embodiment, the transforming may include determining a stabilization conversion formula based on a difference between the coordinates of the corresponding feature points, and converting the coordinates of the first current frame based on the stabilization conversion formula to obtain the converted image, thus leading to stabilization between the first current frame and first previous frame. The stabilization conversion formula may express an average conversion for all corresponding feature points. The conversion formula may include a matrix.

Prior to the identification of the corresponding points, a point may be determined for the converted image using a feature detection algorithm. Determined points are typically corners of the object in the acquired image. This may include corner of the probe, tooth, etc. It may be further determined whether the converted image includes a minimum number of points such as at least 10, preferably at least 20. If not, then a further step of identification for the minimum number points may be performed prior to identification of the corresponding points using the feature detection algorithm such as corner detection algorithm (e.g. Shi-Tomasi corner detection algorithm or Harris corner detection). Furthermore, identification of the corresponding points may be performed by determining a point in the second current frame corresponding to the point of the converted image. This may be performed by utilizing an algorithm such as Lucas-Kanade algorithm, and particularly, sparse iterative version of the Lucas-Kanade optical flow pyramid algorithm. The Lucas-Kanade algorithm may also be based on the luminance I of RGB color model. In an embodiment, the transforming may include determining a stereo conversion formula based on a difference between the coordinates a the corresponding points, and converting the coordinates of the second current frame (or the converted image) based on the stereo conversion formula to obtain a stereo aligned image. The stereo conversion formula may express an average conversion for all corresponding points of the feature points. The conversion formula may include a matrix.

In order to avoid or at least substantially reducing the latency problem, a processor that is comprised in the i) frame, or ii) a mount that is configured to be arranged on the user of the system and in wired connection with the pair of camera and display performs the disclosed stereo alignment and stabilization method. Such processor may include one of Field-Programmable Gate Array (FPGA), Digital Signal Processor, Advanced RISC Machine (ARM) processor, or a combination thereof.

In an embodiment, the processor may be configured to apply magnification in response to a trigger event. The trigger event may include at least one of an input from the user and/or an input signal generated in response to a change in at least one of a position or distance between the at least one camera and intraoral target area. The input from the user may include at least one of a verbal instruction, a physical interaction with the loupe system, or a gesture instruction.

In an embodiment, the system includes a microphone, usually having directionality directed towards the user's mouth, configured to receive the verbal instruction and converting the verbal instructions into electrical signals, and the processor being configured to convert the electrical signals into an operational command for digitally applying the magnification. This is particularly useful because the user may not only focus on the dental procedure but also keep the dental procedure more hygienic as the need of touching any system component during the procedure is avoided. Additionally or alternatively, the system may include a user interface configured to receive the user input through a physical interaction of the user with the system, and the processor being configured to generate an operational command in response to the input for digitally applying the magnification. Additionally or alternatively, the system may include a sensor configured to detect a predefined user gesture and convert the detected gesture into an electrical signal and the processor being configured to convert the electrical signals into an operational command for digitally applying the magnification. The sensor may include an additional camera comprised in the system, the additional camera being configured to detect the gesture such as hand gestures and the processor is configured to receive and correlate the detected hand gestures with magnification commands corresponding to the hand gesture. The magnification commands, corresponding to the hand gesture, is accessible to the processor from a memory. Additionally or alternatively, the sensor may be configured to sense head movements like nodding and accordingly provide a sensor signal to the processor, which is configured to receive and correlate the detected sensor with magnification commands. The magnification commands, corresponding to the head movement, is accessible to the processor from a memory. The system may include a sensor configured to generate the input signal in response to at least one of a relative change in position between the at least one camera and the intraoral target area or a change in distance between the at least one camera and the intraoral target area; and the processor, in response to the input signal, is configured to automatically adjust the applied magnification factor to maintain at least substantially the same magnification of the intraoral target area that was visible prior to the change in position and/or change in distance.

In an embodiment, the processor is configured to automatically identify the tooth such as tooth type in the overlaid virtual content such as the three-dimensional digital representation corresponding to the tooth for which the pocket depth is being measured and highlight one or more points on the gingiva margin where pocket depth measurement is required. The analysis module of the processor may be configured to perform the automatic identification by applying the image processing techniques described earlier such as by using machine learning based identification techniques. Specifically highlighting the points, for example by way of a symbol or color indication, where depth measurement needs to be determined allows for increasing specificity of data gathering points along the gingiva margin. This is particularly useful not only for training new users but also for substantially removing guess work for even an experienced clinician. In an embodiment, one or more points correspond to the points for which historical depth data is available. Having a specific point for depth measurement that relate to historical measurement may be useful in creating a depth profile that may be compared to either a historical depth profile or later with a future depth profile.

In an embodiment, the processor is configured to determine whether the probe tip in the real time image data satisfies a timing criterion, for example whether the probe tip in a sequence of 2D images meets the timing criterion. The timing criterion may include the probe tip staying at least substantially stationary for at least a predefined time period. The processor may apply the image processing techniques to make such a determination, for example by identifying the probe tip in the real time image data and determining movement of the position of the probe tip relative to other object types like gingiva margin in the real time image data. For real time image data comprising the sequence of 2D images, the choice of number of 2D images in the sequence would depend on the frame rate and the predefined time period. The processor may further be configured to extract the at least one 2D image from the real time image data when the probe tip satisfies the timing criterion and/or instruct the at least one camera to capture the at least one 2D image when the probe tip satisfies the timing criterion. This approach allows for ensuring that the determined pocket depth is for a discrete measurement point that is intended for such measurement. Additionally or alternatively, the processor may be configured to receive user input such as via verbal command via the microphone, usually having directionality directed towards the user's mouth, indicating when to capture the at least one 2D image. Such verbal command may be based on when the user thinks the probe tip is positioned at the discrete measurement point along the gingiva margin satisfying the timing criterion.

In an embodiment, the processor is configured to determine whether the probe tip in the real time image data satisfies a local minima criterion, for example the probe tip in a sequence of 2D images meets the local minima criterion. The local minima criterion may include the probe tip representing maximum insertion length for a discrete measurement point when compared to the insertion length for measurement points in the neighborhood of the discrete measurement point. The range of neighboring measuring points along the gingiva margin may be predefined in the system or may be defined by the user. The processor may apply the image processing techniques to make the determination, for example by identifying the probe tip in the real time image data and determining in which of the 2D images of the sequence (representing real time image data), the length of the probe tip is the least visible outside the periodontal pocket, i.e. representing the maximum insertion length. The processor may further be configured to extract the at least one 2D image from the real time image data when the probe tip satisfies the local minima criterion and/or instruct the at least one camera to capture the at least one 2D image when the probe tip satisfies the local minima criterion. This approach allows for ensuring that the determined pocket depth is for a discrete point that is intended for the measurement. Additionally or alternatively, the processor may be configured to receive user input such as via verbal command via a microphone, usually having directionality directed towards user's mouth, indicating when to capture the at least one 2D image. Such verbal command may be based on when the user thinks the probe tip is positioned at the discrete measurement point along the gingiva margin satisfying the local minima criterion.

In an embodiment, the processor is configured to identify the discrete measurement point where at least one of the timing criterion, or local minima criterion is satisfied, compare whether the identified discrete measurement point differs from the one or more points on the gingiva margin where pocket depth measurement is required such as the one or more points highlighted on the virtual content such as the three dimensional digital representation, and replacing the at least one of the one or more discrete points, e.g. highlighted points, on the gingiva margin with a point on the virtual content corresponding with the identified discrete measurement point. The skilled person would appreciate that such replacement is performed taking into account correspondence between the point that is being replaced (at least one of the one or more discrete points) and the point that is making the replacement (discrete measurement point), i.e. mesiobuccal may be replaced by a discrete measurement point closest to the mesiobuccal, oral may be replaced by a discrete measurement point closest to the oral, and likewise. The processor may further be configured to highlight the discrete measurement points on the gingiva margin in the represented virtual content for any future pocket depth measurement.

In an embodiment, the processor is configured to generate a new measurement guideline, as part of the virtual content, corresponding to the discrete measurement point. The discrete measurement points are points that satisfy at least one of the timing criterion or local minima criterion. The processor may further be configured to receive the new measurement guidelines and overlay the new measurement guideline over the real time image data such that at least a portion of the real time image data is viewable, through the overlaid new measurement guideline, on the display unit in real time. Such overlay may include at least one of an overlaid guideline or a temporary overlaid guideline as described earlier. Because the processor is configured to identify object types such as probe tip, the processor is configured to track the periodontal probe utilizing the image processing techniques and determine, based on the new measurement guidelines, whether the probe tip is angled/oriented correctly for a reliable measurement. As the processor is configured to recognize the tooth type and the discrete measurement point in relation to the gingiva margin and tooth type, the processor may be configured to generate the new measurement guidelines using clinical rules. For example, the processor is configured to generate guidelines that, for a specific discrete point, requires the probe tip to be parallel to the long axis of the tooth. Alternatively, the processor is configured to access new measurement guideline from a database that stores, usually clinically complying, new measurement guidelines for specific points such as discrete measurement points along the gingiva margin for a specific tooth type.

In an embodiment, the processor is configured to automatically identify the tooth such as tooth type in the three-dimensional digital representation corresponding to the tooth for which the pocket depth is being measured with or without identification of actual tooth position in mouth .e. tooth number according to some tooth numbering scheme; and to digitally represent on the three-dimensional digital representation at least one historical depth of the periodontal probe at one or more points or along the entire gingiva margin or a portion of the gingiva margin. The analysis module of the processor may be configured to perform the automatic identification by applying the image processing techniques described earlier such as machine learning based identification. The processor may further be configured to superimpose the determined depth, which may include the entire depth profile, on the three-dimensional digital representation in order to digitally represent the depth on the three-dimensional digital representation. In one embodiment, the digitally represented depth on the three-dimensional digital representation may be stored as a three-dimensional patient record such as a patient specific dental chart. Additionally or alternatively, the processor receives the digitally represented depth on the three-dimensional digital representation and overlays the three-dimensional digital representation with digitally represented depth over the real time image data such that at least a portion of the real time image data is viewable, through the overlaid three-dimensional digital representation, on the display unit in real time. The overlaying may be implemented in accordance with the image registration technique described earlier. Having such an overlay allows the user to monitor patient pocket depth information/dental condition in real time.

In an embodiment, the probe includes a force sensitive mechanism such as a spring mechanism that is operationally engaged with a probe element. When the probe tip is pushed inside the pocket depth and a predefined insertion force is reached, the spring mechanism applies a force on the probe element that gets displaced/deviated, thus representing a variation of the probe element. The processor is configured to determine such variation, using image processing techniques, in the captured at least one 2D image and/or real time image date, indicating that the predefined insertion force for making pocket depth measurement is applied. Using this approach on representation of the probe element in the at least one 2D image and/or real time image data force ensures that all the pocket depth measurements are made under the same force conditions and variability introduced in force application across different users may be at least substantially avoided. The at least one 2D image captured where the processor determines such displacement (variation) of the probe element is usually used for determining the periodontal pocket depth.

In an embodiment, the processor is configured to access the probe profile comprising a digital variation of a probe element when the predefined insertion force is applied; apply the image processing technique comprising assessing the information, from at least one 2D image, about the probe element in relation to the digital variation; determine whether the predefined insertion force is applied. The analysis module may be configured to makes such determination. The analysis module may apply, earlier described, image processing technique to compare the captured at least one 2D image with the probe profile to identify if the probe element as represented in the at least one 2D image matches with the probe element as represented in the probe profile, which comprises the digital variation as a feature on a 2D image. If not, then the processor is configured instruct the at least one camera to capture an additional at least one 2D image until a match is identified between the probe element as represented in the additional at least one 2D image matches and the probe element as represented in the probe profile. The skilled person would realize that it is possible to have the at least one 2D image satisfying the matching criterion with the probe profile, in which case it is not necessary to have the first step of mismatch.

In an embodiment, the digital variation may include geometrical information of the probe element when the variation occurs, and the processor may be configured to determine, based on a geometrical comparison, whether a match between the probe element identified from the at least one 2D image and the geometrical information exists. Additionally or alternatively, the digital variation may include an angular information between the displaced probe element and another part of the probe when the variation occurs, and the processor may be configured to determine whether a match between i) an angle that the probe element makes with another part of the probe, as represented in the at least one 2D image, and ii) the angular information. In another embodiment, the probe element includes an LED on the probe, the LED being configured to light up when the predefined insertion force is applied. The digital variation includes change of the LED from switched OFF to switched ON state. The processor is configured to determine, by performing pixel comparison, whether state of LED from the at least one 2D image represents pixel of the LED in switched ON state, as included in the probe profile. In any of these embodiments, if the match exists, the processor identifies that the predefined insertion force is applied and the at least one 2D image used for determining the match may be used for determining the pocket depth.

Thus, according to an embodiment, the processor is configured to capture the at least one 2D image from the real time image data when the determination is made that the predefined insertion force is applied. Additionally or alternatively, the processor is further configured to provide a feedback to the user of the periodontal probe in accordance with the determination, usually in real time during the insertion of the periodontal probe tip in the pocket. Such feedback may include an audio message indicating that the measurement was successfully taken. In some scenarios, the feedback may include an audio message indicating that more force on the tip should be applied. Using such determination and/or feedback in real time allows for making measurements under the same force condition, thereby increasing accuracy of measurements and also avoids a scenario where the user applies excessive force that may result in a painful experience for the patient.

According to an embodiment, a computer program product embodied in a non-transitory computer readable medium is disclosed. The computer program product includes computer readable program code being executable by a hardware data processor to cause the hardware data processor to perform a method when said computer readable program code is executed by the hardware data processor. The method may include one or more functions that any of the system components such as analysis module, stabilization module, registration module, processor, etc. are configured to perform according to any of the disclosed embodiments. For example, when the computer readable program code is executed by the hardware data processor, the hardware data processor is configured to instruct at least one camera that is attached to a frame to capture at least one 2D image of the intraoral target area, to receive the captured at least one 2D image and to process the captured at least one 2D image of the intraoral target area. For example, such processing may include determining, in relation to the gingiva margin, an insertion length of the probe tip in the periodontal pocket by applying an image processing technique on information obtained about the probe tip in the captured at least one 2D image. The determined insertion length represents the depth of the periodontal pocket. The method performed by the hardware data processor disclosed in this embodiment is configured to include one or more of the embodiments that are disclosed later.

According to an embodiment, a method for determining loss of attachment is disclosed. The method includes receiving at least one 2D image using at least one camera; determining, using an image processing technique on the at least one 2D image, i) a periodontal pocket depth, ii) whether a gingival recession has occurred, iii) a gingival recession if the determination is made that the gingival recession has occurred, and iv) the loss of attachment based on a combination of the determined periodontal pocket depth and the determined gingival recession. The determination of whether the gingival recession has occurred may be for a discrete point along the gingiva margin where the measurement is made and based on a distance between a cementoenamel junction and the gingiva margin. If the determination is made that no gingival recession has occurred, the gingival recession is zero and the loss of attachment equals to the determined pocket depth.

According to an embodiment, a computer implemented method for measuring a depth of a periodontal pocket defined by a gap between a tooth and gingiva is disclosed. The method includes capturing at least one 2D image of an intraoral target area, the at least one 2D image including a representation of at least a part of the tooth, a gingiva margin defined by a section of the gingiva adjacent to the at least a part of the tooth, and a probe tip when the probe tip is inserted into the periodontal pocket. The capturing may be performed by at least one camera that is attached to a frame, which is configured to be worn by a user. The method further includes determining, in relation to the gingiva margin, an insertion length of the probe tip in the periodontal pocket by applying an image processing technique on information obtained about the probe tip in the captured at least one 2D image, wherein the determined insertion length represents the depth of the periodontal pocket. The method may include any functions that any of the system components such as analysis module, stabilization module, registration module, processor, etc. are configured to perform according to any of the disclosed embodiments.

BRIEF DESCRIPTION OF THE DRAWINGS

The Embodiments of the Disclosure, Together with its Advantages, May be Best Understood from the Following Illustrative and Non-Limiting Detailed Description Taken in Conjunction with the Accompanying Figures in which

FIG. 4A illustrates a front view of a periodontal probe when in use for measuring at least a periodontal pocket depth according to an embodiment;

FIG. 4B illustrates a side view of the periodontal probe when in use according to the embodiment of FIG. 4A;

FIG. 5A illustrates a front view of a periodontal probe when in use for measuring at least a periodontal pocket depth according to an embodiment;

FIG. 5B illustrates a side view of the periodontal probe when in use according to the embodiment of FIG. 5B;

FIG. 8 illustrates different orientations of a periodontal probe according to an embodiment;

FIG. 9 illustrates different orientation of a periodontal probe according to an embodiment;

FIG. 13A illustrates a probe element according to an embodiment;

FIG. 13B illustrates the probe element of FIG. 13A in a displaced position according to an embodiment;

DETAILED DESCRIPTION

In the following description, reference is made to the accompanying figures, which show by way of illustration how the invention may be practiced.

Figure 1:
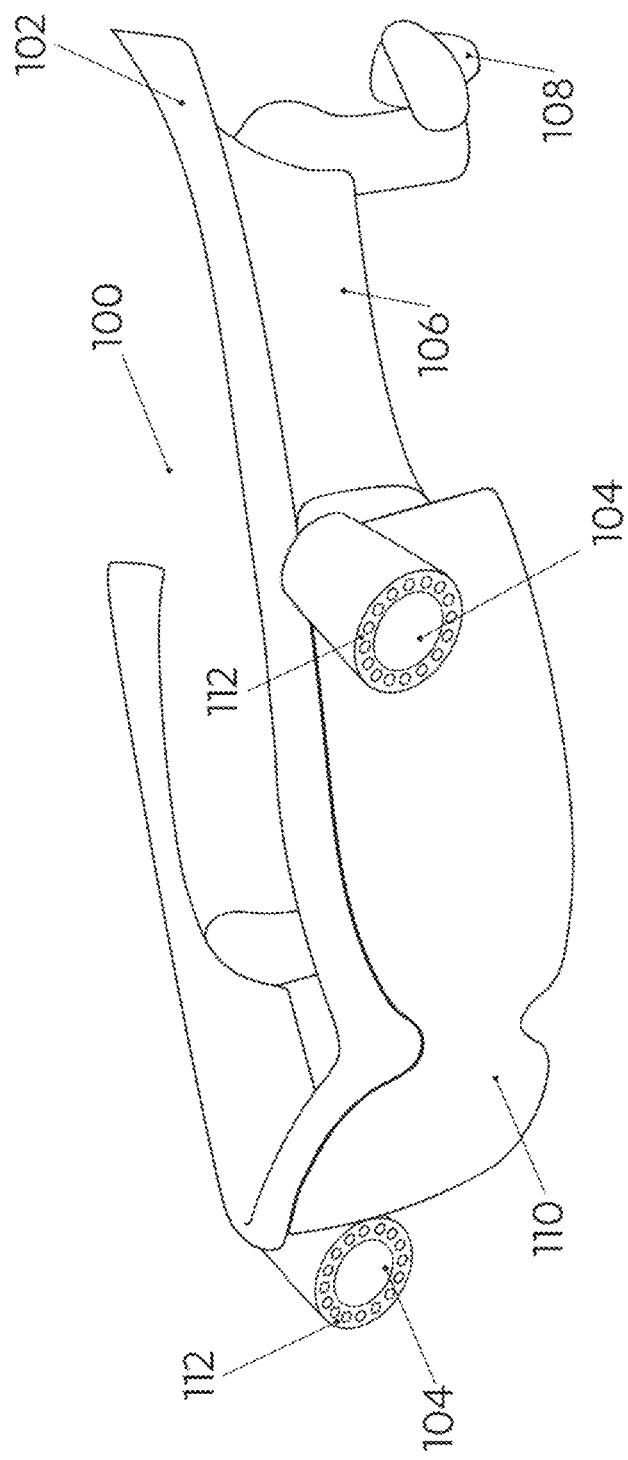
FIG. 1 illustrates a system according to an embodiment.

FIG. 1 illustrates a system according to an embodiment. The system 100 includes a frame 102, at least one camera 104, and a processor 106. The frame is configured to be worn by a user (202, FIG. 2). The at least one camera 104 is attached to the frame 102 and configured to capture at least one 2D image (FIG. 3B or FIG. 6B) of an intraoral target area. The at least one 2D image includes a representation of at least a part of the tooth (322, FIG. 3), a gingiva margin (316, FIG. 3) defined by a section of the gingiva ((310, FIG. 3) adjacent to the at least a part of the tooth, and a probe tip (312, FIG. 3) when the probe tip is inserted into the periodontal pocket (412, FIG. 4; 512, FIG. 5). The processor 106 is configured to receive the captured at least one 2D image. The processor is further configured to determine, in relation to the gingiva margin, an insertion length (406, FIG. 4; 512, FIG. 5) of the probe tip in the periodontal pocket by applying an image processing technique on information obtained about the probe tip in the captured at least one 2D image. The determined insertion length represents the depth of the periodontal pocket (412, FIG. 4). The system, which may be a digital dental loupe system, disclosed in this embodiment is configured to include one or more of the disclosed embodiments. For example, the system may further include other elements such as one or more of i) a display 110 that is configured to display at least one of the at least one 2D image or real time image data, with or without the virtual content, ii) at least one light source 112 that is configured to illuminate the intraoral target area of a patient, iii) a speaker module 108 that is configured to deliver notifications such as audio messages, iv) a microphone (1220, FIG. 12) that is configured to receive voice commands/verbal instruction from the user, or v) a communication module (1204, FIG. 12) to transmit to and/or receive digital data from other devices such a database that may store recorded images, a remote processing unit (1230, FIG. 1230). The system may include a memory (1214, FIG. 12) that may store the depth profile, digital profile. Alternatively, the communication module may receive the virtual content and/or digital profile from other devices such as a remote database (1228, FIG. 12) which may be considered part of the system) and such received virtual content and/or digital profile may be accessed by the processor.

In different embodiments, the at least one camera is illustrated to be attached at the distal end of the frame, but it is within the scope of the invention to have the at least one camera closer to each other, for example, spatially separated by a known distance but closer and on either side of the center of the frame.

Figure 2:
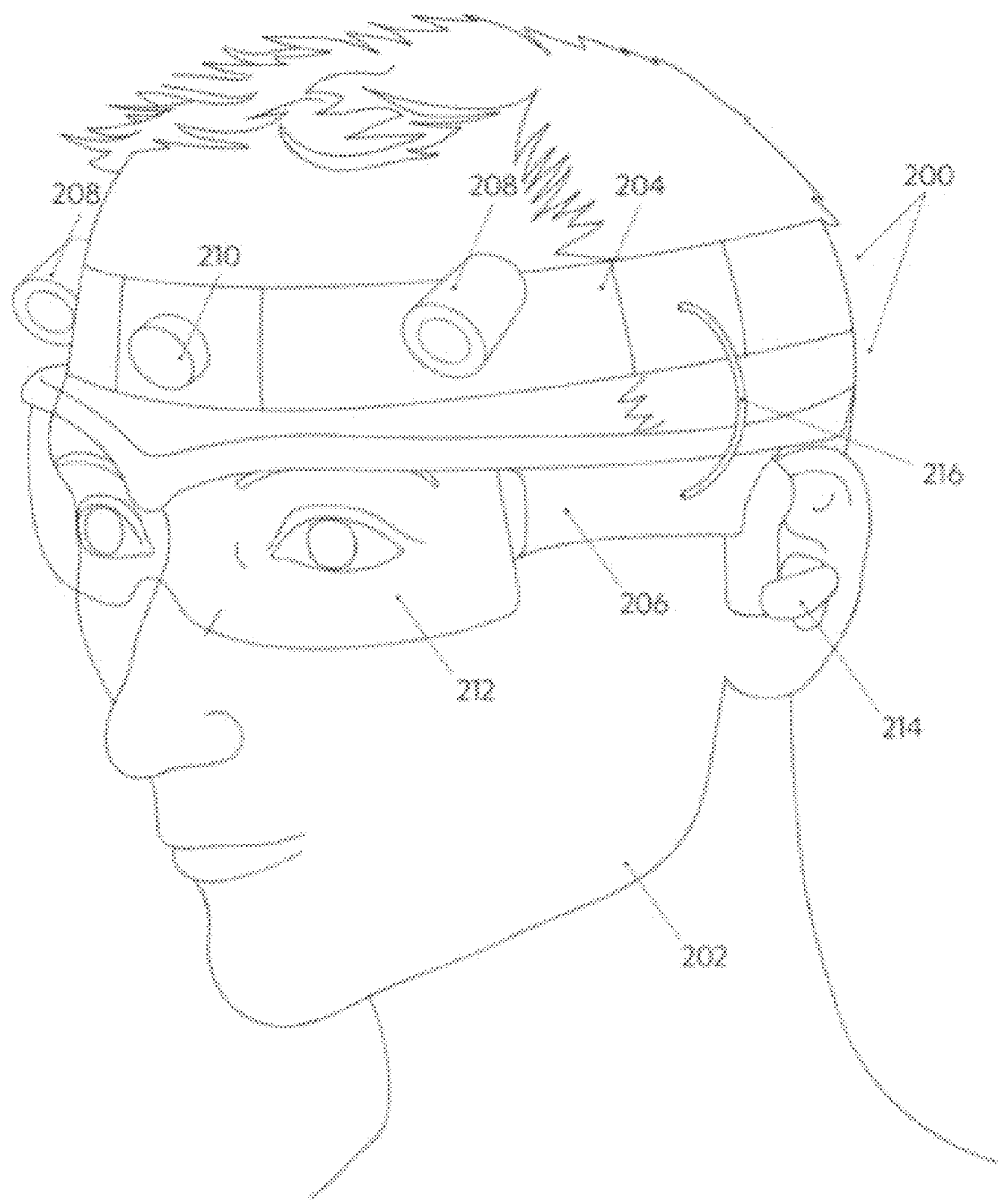
FIG. 2 illustrates a two-part system mounted on the user according to an embodiment.

FIG. 2 illustrates a two-part system mounted on the user according to an embodiment. This embodiment includes same elements shown in embodiment of FIG. 1 and the functionalities of these elements are same as well. However, the two embodiments differ in arrangement of the elements. FIG. 1 illustrates a single part system whereas FIG. 2 illustrates a two parts system 200 where the two parts are detachably connectable to one another. In this scenario, the frame includes a first part that may be eyeline mounted unit 206 and the other part includes a head mounted unit like a band 204. The head mounted unit 204 may include the at least one camera 208, a light source 210 and the eyeline mounted unit includes a display 212, a processor, a speaker 214. The frame is wearable by the user 202. The detachably connected refers to the two parts being at least communicatively connected such as by a wireless link. But, the communication connectivity between the multi-parts may include a physical connection 216 as illustrated in the FIG. 2. The multi part system may further include other elements such as a microphone, communication module, memory etc. as in the case of embodiment of FIG. 1. The skilled person would realize that the arrangement of different elements of the system may be varied so long as the functionality of the elements and functional relationship, as disclosed herein, is maintained. For example, the processor may be removed from the frame and may include a body worn like a belt worn processor that can be worn around the user's waist. This results in creating a light weight frame, which may be particularly useful for users using the system (e.g. dental loupe system) on a regular basis such as many hours per day.

Figures 3A, 3B:
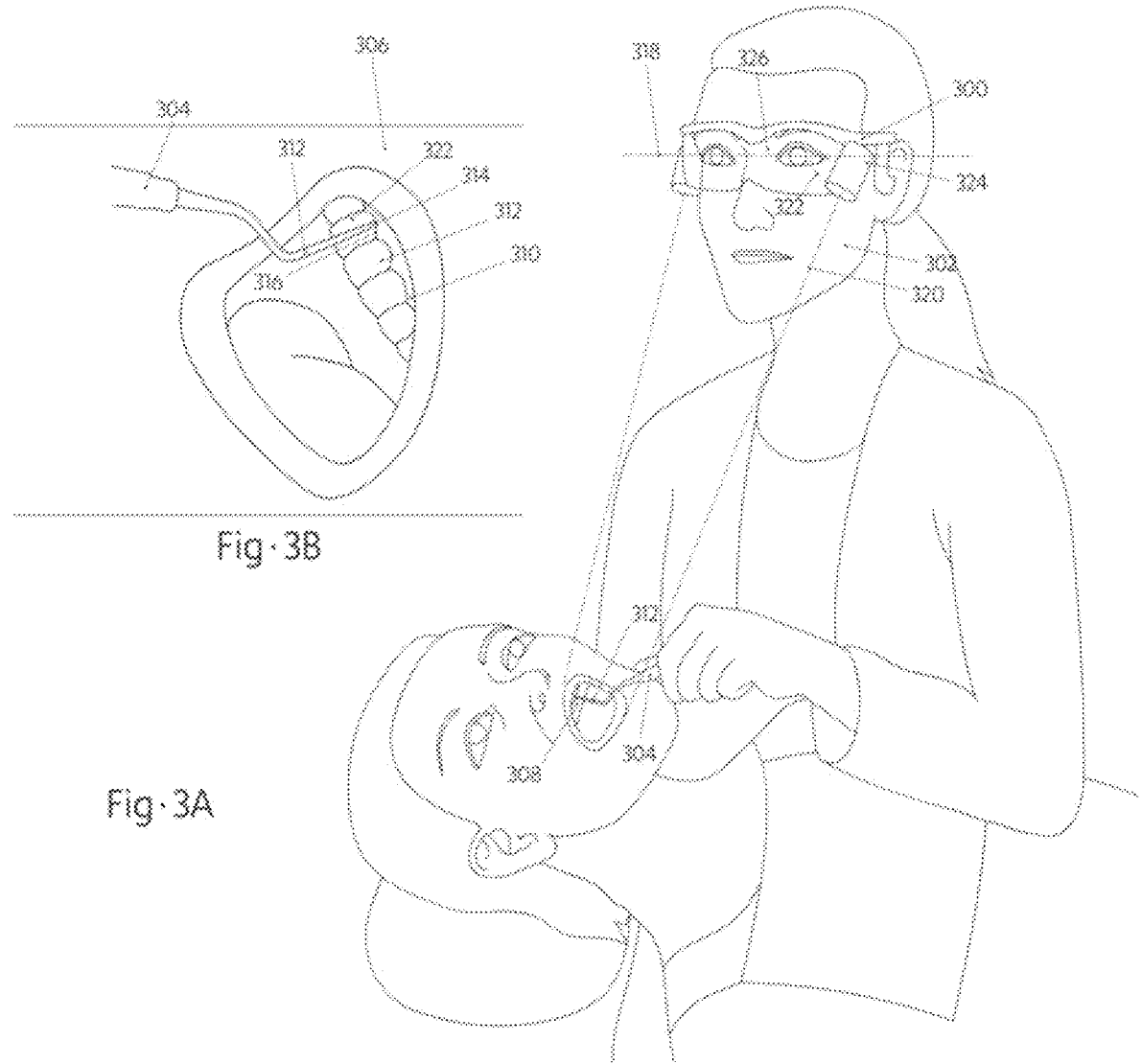
FIG. 3A illustrates a system when worn by the user according to an embodiment.
FIG. 3B illustrates a blown-up view of a real time image data according to the embodiment of FIG. 3A.

FIG. 3A illustrates a system when worn by the user according to an embodiment and FIG. 3B illustrates a blown-up view of a real time image data according to the embodiment of FIG. 3A. The system 300 is configured to be worn by the user 302. As shown the at least one camera 324 is arranged on the frame such that an optical axis 320 of the at least one camera is below a reference line 318. In other words, the at least one camera 324 is arranged on the frame such that an imaging angle 322 between the reference line 318 and the optical axis 320 is defined by an angle 322 that keeps user's view of the display at least substantially straight in line with the reference line 318 when the frame is worn by the user while the optical axis 320 is directed towards the intraoral target area 308. This allows the user to see the at least one 2D image 306 and/or real time image data 306 on the display 326 without a need for the user to round his back by bending forward and drawing his shoulders forward to capture the at least one 2D image and/or real time image data. The at least one 2D image and/or real time image data 306 includes representation of the probe 304, probe tip 312, at least a part of the tooth 322 for which at least a periodontal pocket depth at a discrete point 314 is being measured, gingiva margin 316 defined by the intersection of the gingiva 310 and the tooth 322. This embodiment discloses a scenario where the at least one 2D image and/or real time image data represents at least a part of facial side of the tooth that is typically accessible in a direct field of the view of the at least one camera.

FIG. 4A illustrates a front view of a periodontal probe when in use for measuring at least a periodontal pocket depth according to an embodiment, and FIG. 4B illustrates a side view of the periodontal probe when in use according to the embodiment of FIG. 4A. The embodiment shows a gingiva 402 where a gingiva margin 404 related to a discrete point for a tooth 414 has not recessed. Therefore, the periodontal pocket depth 406 for a periodontal pocket 412 represents loss of attachment and no gingival recession. The insertion length of a probe tip 410 of the probe 408 represents the periodontal pocket depth 406.

FIG. 5A illustrates a front view of a periodontal probe when in use for measuring at least a periodontal pocket depth according to an embodiment, and FIG. 5B illustrates a side view of the periodontal probe when in use according to the embodiment of FIG. 5B. The embodiment shows a gingiva 506 where a gingiva margin 502 related to a discrete point for a tooth 508 has recessed resulting in a recessed gingiva margin 504. Therefore, loss of attachment is represented by a combined length of the gingival recession 510 and periodontal pocket depth 512. In this case, 502 also represents a cementoenamel junction and the distance between the cementoenamel junction where the unreceesed gingiva 518 was present, and the recessed gingival margin 504 represents the gingiva recession 510 in comparison to the unrecessed gingiva 518. The insertion length of a probe tip 516 of the probe 514 represents the periodontal pocket depth 512.

Figures 6A, 6B:
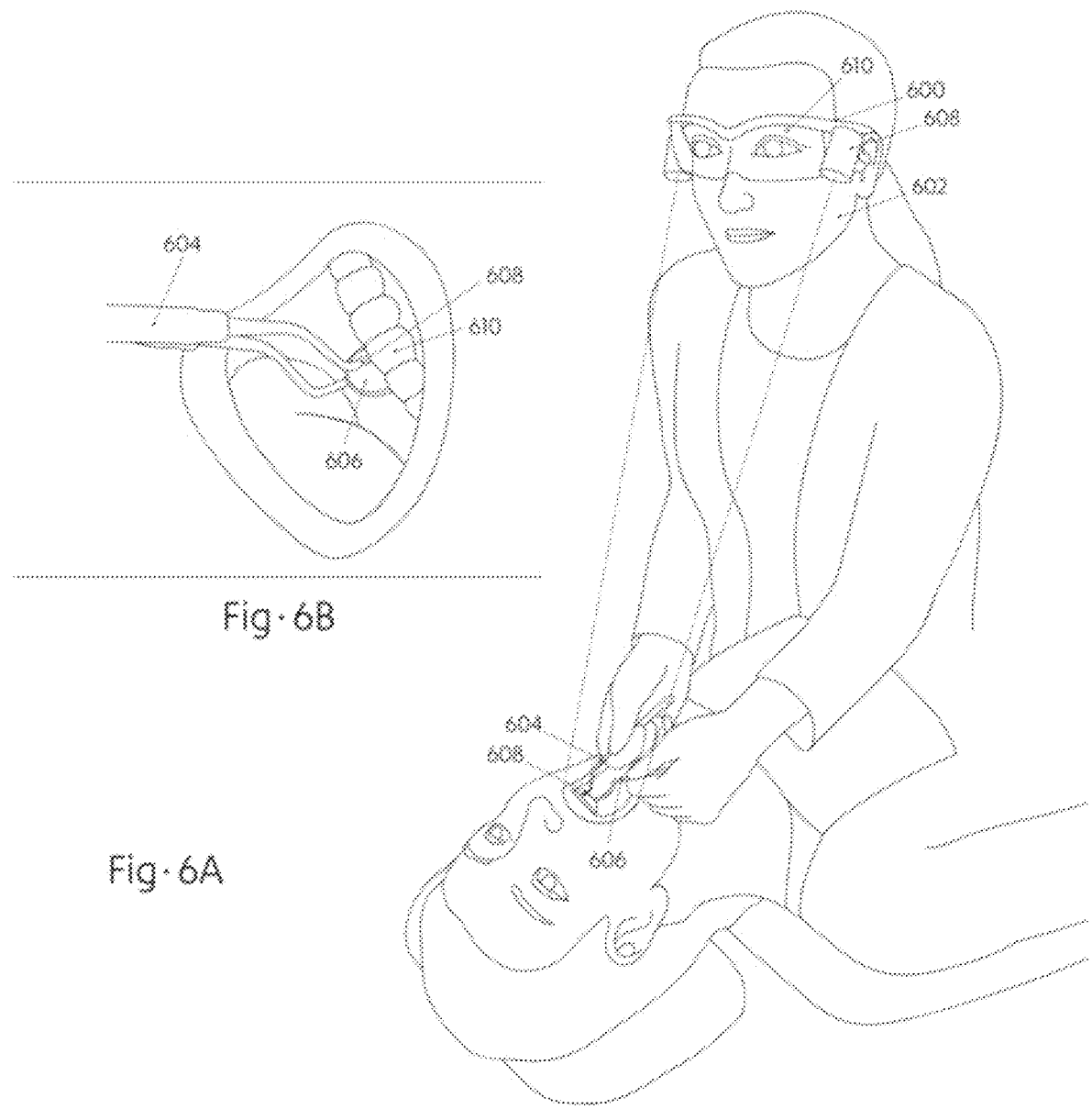
FIG. 6A illustrates a system when worn by the user according to an embodiment.
FIG. 6B illustrates a blown-up view of a real time image data according to the embodiment of FIG. 6A.

FIG. 6A illustrates a system when worn by the user according to an embodiment and FIG. 6B illustrates a blown-up view of a real time image data according to the embodiment of FIG. 6A. This embodiment is substantially same with the embodiment disclosed in FIG. 3A and FIG. 3B except that this embodiment describes a scenario where the at least one camera 608 is configured to capture at least one 2D image and/(FIG. 6B) or real time image data (FIG. 6B) relating to intraoral areas that are at least substantially inaccessible or inconveniently accessible in the direct field of view of the at least one camera 608 from a reflection of these intraoral areas and the probe tip 608 of the probe 604 from a mouth mirror 606. The mouth mirror that is configured to provide an indirect vision, to the at least one camera. Such areas may include one or more of i) surfaces on the lingual or palatal side such as tooth 610 surface, or ii) gingiva adjacent to the tooth surface and probe tip when the probe tip is inserted into the periodontal pocket on the lingual or palatal side. The system 600 is configured to be worn by the user 602. The captured at least one 2D image and/or real time image data is visible on the display 610. In this embodiment, the at least one camera 608 is arranged on the frame such that an optical axis of the at least one camera is below the reference line.

Figures 7C, 7D:
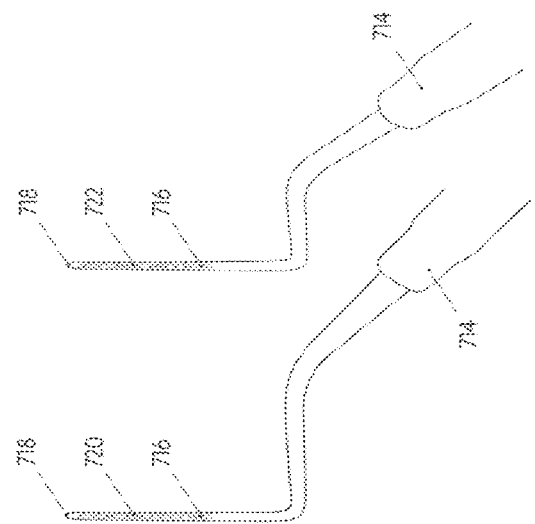
FIG. 7C illustrates a periodontal probe viewed from a first perspective according to an embodiment.
FIG. 7D illustrates the periodontal probe, viewed from a second perspective, according to the embodiment of FIG. 7C.
Figure 7B:
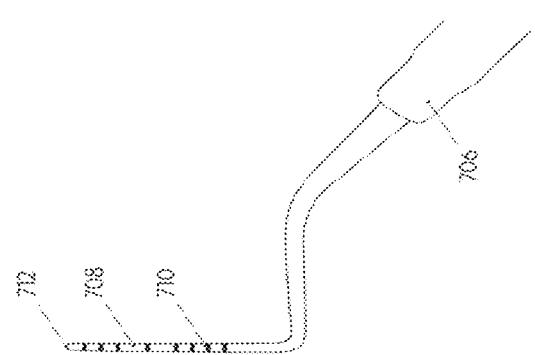
FIG. 7B illustrates a periodontal probe according to an embodiment.
Figure 7A:
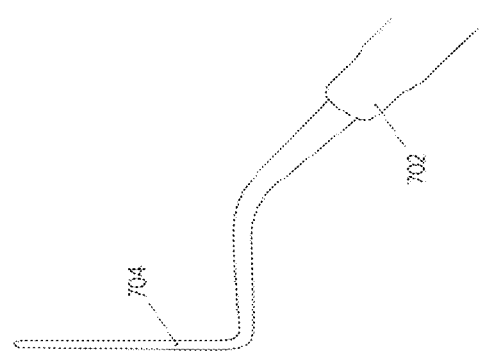
FIG. 7A illustrates a periodontal probe according to an embodiment.

FIG. 7A illustrates a periodontal probe 702 according to an embodiment. The probe tip 704 is devoid of any marking such as devoid of depth markers or fiducial markers, i.e. the probe does not include any indication of length from the distal point of the probe tip to a point along length of the probe tip. The information obtained about the probe tip in the captured at least one 2D image includes a geometrical information about the probe tip with or without any other part of the probe. Such geometrical information represents representation of the probe from a specific viewpoint/perspective.

FIG. 7B illustrates a periodontal probe 706 according to an embodiment. The probe tip 708 includes depth markers 710, which typically include either color coded marking, graduated marking or any other indicators representing length between a distal point 712 of the probe tip and a plurality of depth markers of the probe tip. The person skilled in the art may envisage a number of different visual markings, including but not limited to, different shapes, widths, colors, etc. that provide the same function as the depth markers, i.e. an indication between the distal point 712 of the tip 708 to these depth markers. The information obtained about the probe tip in the captured at least one 2D image includes a digital representation of at least one depth marker comprised in the probe tip.

FIG. 7C illustrates a periodontal probe 714 viewed from a first perspective according to an embodiment. FIG. 7D illustrates the periodontal probe 714 according to the embodiment of FIG. 7C, except in this embodiment, the probe is shown from a second perspective that is different from the first perspective. The probe tip 716 or any other probe part may include fiducial markers 720. The fiducial markers of at least one of pattern, size, shape, color preferably different and more preferably contrasting with colors present in the intraoral target area or any combination thereof. The representation of the fiducials markers is a function of the perspective view of the probe tip or any other part that includes such fiducial markers, i.e. the fiducial markers that are visible from one perspective is different from those visible from a different perspective. This is particularly useful in determining orientation of the periodontal probe 714 when in use. The representation of the fiducial markers visible outside the periodontal pocket may also be useful in determining the insertion length because the representation of the fiducial markers indicates the distance between a distal tip 718 and the visible representation of the fiducial markers. Similarly, the representation of the fiducial markers that align with the cementoenamel junction may also be useful in determining the gingival recession because the representation of the fiducial markers is indicative of the distance between different points along the probe tip 716.

FIG. 8 illustrates different orientations of a periodontal probe according to an embodiment. The intraoral target area, as represented in the at least one 2D image, is represented by the tooth 802, gingiva 804, gingiva margin 806, and the probe in one of the different orientations. As illustrated, the different orientations of the probe 808, 808', 808" may include a first orientation 810, a second orientation 810' and a third orientation 810" respectively. The processor is configured to compare, for each discrete point, each of these different orientation views (perspectives) with the digital probe profile such as distinct projected views of the probe profile and determine whether the orientation is optimum for a correct measurement of the pocket depth, as described earlier. If not, then the processor may be further configured to instruct a notification module such as through an audio message delivered via the speaker to notify the user of the discrepancy. The user may change the orientation for taking another measurement until an optimum orientation for taking the measurement is achieved.

FIG. 9 illustrates different orientation of a periodontal probe according to an embodiment. The intraoral target area, as represented in the at least one 2D image, is represented by the tooth 902, gingiva 904, gingiva margin 906, and the probe in one of the different orientations, the probe includes fiducial markers. As illustrated, the different orientations of the probe 908, 908', 908" may include a first orientation 910, a second orientation 910' and a third orientation 910" respectively. The processor may be configured to compare, for each discrete point, each of these different orientation views (perspectives) with the digital probe profile such as distinct projected views of the probe profile and determine whether the orientation is optimum for a correct measurement of the pocket depth, as described earlier. Additionally or alternatively, because the probe includes fiducial markers 912, 912', 912" which are unique to a specific perspective of the probe, the processor is configured to determine whether orientation of the probe is optimum for pocket depth measurement by comparing, for a discrete point, the identified fiducial marker with the distinct fiducial marker(s) of the digital probe profile. If not, then the processor may be further configured to instruct a notification module such as through an audio message delivered via the speaker to notify the user of the discrepancy. The user may change the orientation for taking another measurement until an optimum orientation for the measurement is achieved. The representation of the fiducial markers 912, 912', 912" visible outside the (recessed or unrecessed) periodontal pocket may also be useful in determining the insertion length because the representation of the fiducial markers indicates the distance between a distal tip and the visible representation of the fiducial markers. Similarly, the representation of the fiducial markers that align with the cementoenamel junction 916 at the discrete point where measurement is made may also be useful in determining the gingival recession because the representation of the fiducial markers is indicative of the distance between different points along the probe tip.

Figure 10:
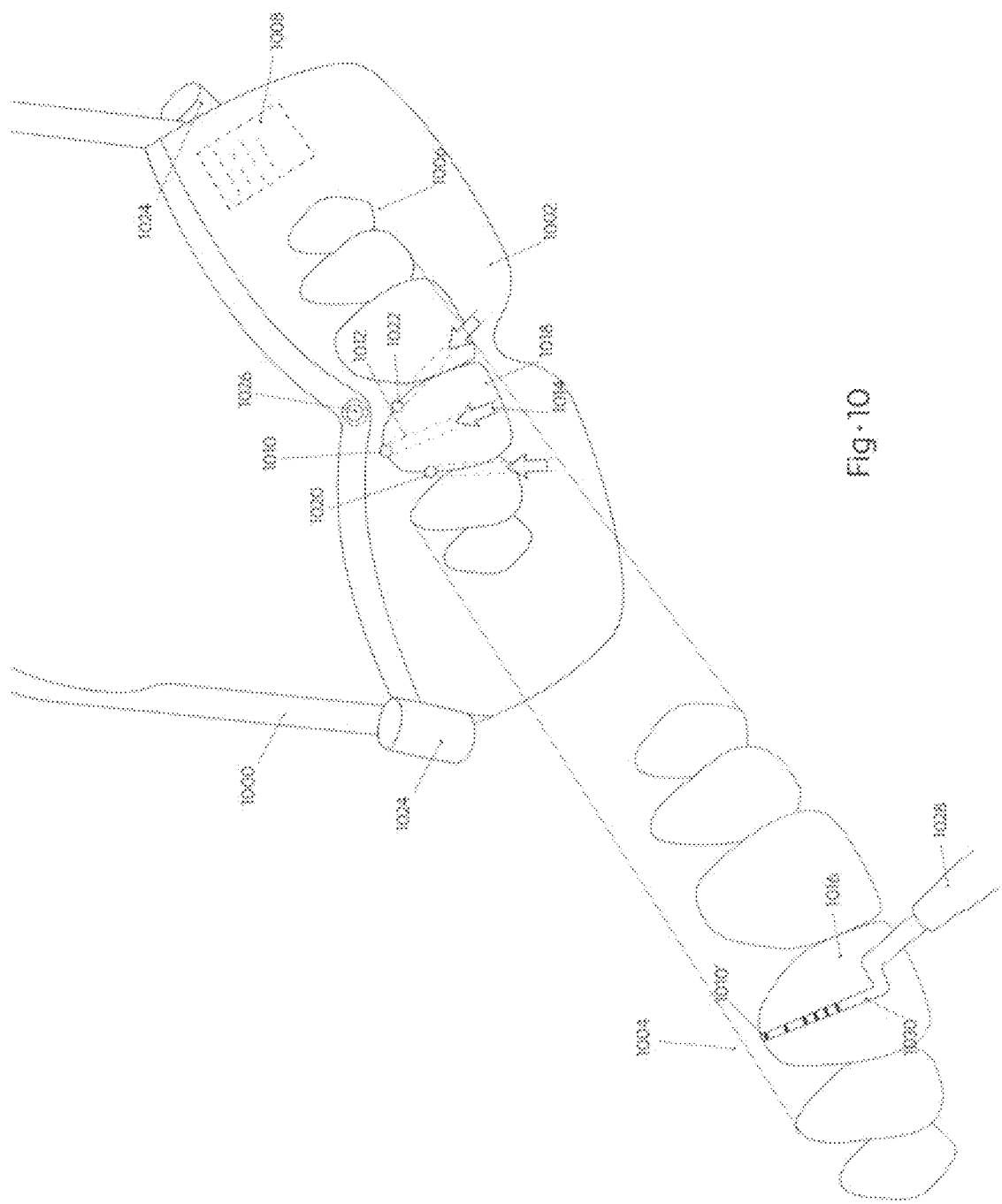
FIG. 10 illustrates overlay of a virtual content over a real time image data according to an embodiment.

FIG. 10 illustrates overlay of a virtual content over a real time image data according to an embodiment. The system 1000 includes at least a light source 1026, at least one camera 1024, and a display 1002. The at least one camera is configured to capture real-time image data 1004 of the intraoral target area. The processor is configured to receive a virtual content 1006/1008 such as a three-dimensional digital representation 1006 of at least the tooth with or without the cementoenamel junction and gingiva margin and overlaying the virtual content such as the three-dimensional digital representation over the real time image data such that at least a portion of the real time image data is viewable, through the overlaid three-dimensional digital representation, on the display unit 1002 in real time. For convenience of illustration, the real time image data 1004 and virtual content 1006 are represented separately but, the two data 1004 and 1006 are displayed on the display with the virtual content being overlaid over the real time image data. Having the overlaid virtual content allows for easily establishing a correspondence between the real time image data, i.e. the physical world and any digital information that may relate to the patient. The real time image data 1004 may include representation of the tooth 1016, probe 1028, probe tip 1030 when the tip is inserted into the pocket at a discrete point 1010'. In an embodiment, the overlaying includes positioning a non-structural virtual content 1008 on a section of the display 1002 such that the non-structural virtual content is positioned to avoid an overlap or interference with at least a part of the representation, on the display, of the intraoral target area where a dental procedure such as periodontal pocket measurement is performed. Additionally or alternatively, the processor is configured to perform image registration (spatial and preferably temporal as well) between the real time image data 1004 and the virtual content 1006 such as three dimensional digital representation of the patient's oral cavity. Such registration allows for generating the visual overlay where corresponding points of the virtual content such as the three-dimensional digital representation are aligned with at least a part of the real-world image data such as aligning tooth 1016 of the real time image data with the tooth 1018 of the three-dimensional digital representation. The processor may be configured to track the a spatial and/or temporal change between the virtual content and the real time image data and automatically maintain registration between the virtual content and the real time image data.

The virtual content 1006 may also include highlighted discrete points (1010 corresponding to the discrete real time image data discrete point 1010', 1020, 1022) where the pocket depth measurements in the intraoral cavity are to be taken. The highlighted discrete points in the virtual content 1006 allow the user to precisely identify the measurement points along the gingiva margin. As part of the virtual content 1006, the processor is configured to generate a measurement guideline 1012, preferably for each discrete point, with or without an indication of an arrow 1014. For example, measurement guideline 1012 for discrete point 1010 in the virtual content corresponds to the discrete points 1010' in the intraoral target area. In this embodiment, the overlaid guidelines include a line(s) indicating a desired direction of insertion of the probe tip along the tooth. Because the measurement guideline provides an indication of how the probe tip needs to be angled/oriented in order to make an accurate depth measurement, the measurement guideline may be considered as an overlaid virtual indicator for performing a guided measurement of pocket depth.

Figure 11:
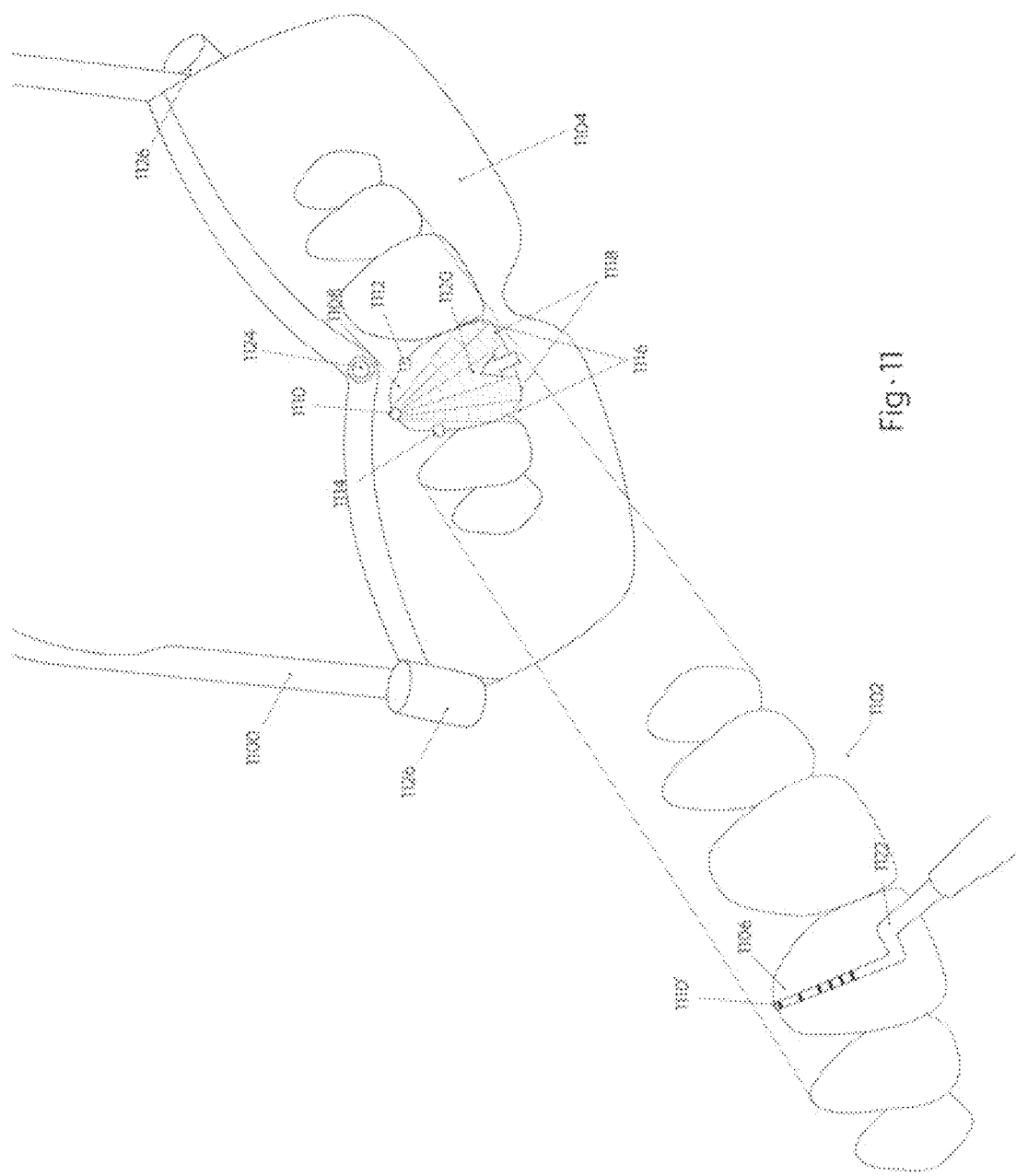
FIG. 11 illustrates overlay of a virtual content over a real time image data according to an embodiment.

FIG. 11 illustrates overlay of a virtual content over a real time image data according to an embodiment. FIG. 11 illustrates essentially the same embodiment as the embodiment of FIG. 10, where 1100 represents the system; 1102 represents a real time image data comprising a tooth 1106, a probe 1122, a discrete point 1110' in the intraoral target area; 1104 represents a virtual content comprising three-dimensional digital representation of the patient's teeth comprising a tooth 1108 and highlighted discrete points (1112, 1114, 1110 corresponding to the discrete point 1110') for which the measurements need to be taken. The processor is configured to perform image registration (spatial and preferably temporal as well) between the real time image data and the virtual content such as three-dimensional digital representation of the patient's oral cavity and overlay corresponding points of the virtual content in an aligned manner with at least a part of the real-world image data. The processor may be configured to track the a spatial and/or temporal change between the virtual content and the real time image data and automatically maintain registration between the virtual content and the real time image data. The processor may further be configured to generate a measurement guideline, as part of the overlaid virtual content, corresponding to at least one of the discrete points. However, in this embodiment, such measurement guidelines include different zones 1116, 1118, 1120 such as permanent or temporary colored zones, for example a red zone 1116 representing wrong insertion, a green zone 1120 representing correct insertion, and an orange zone 1118 representing a transition between wrong and correct insertion. 1126 represents at least one camera and 1124 represents at least one light source.

Figure 12:
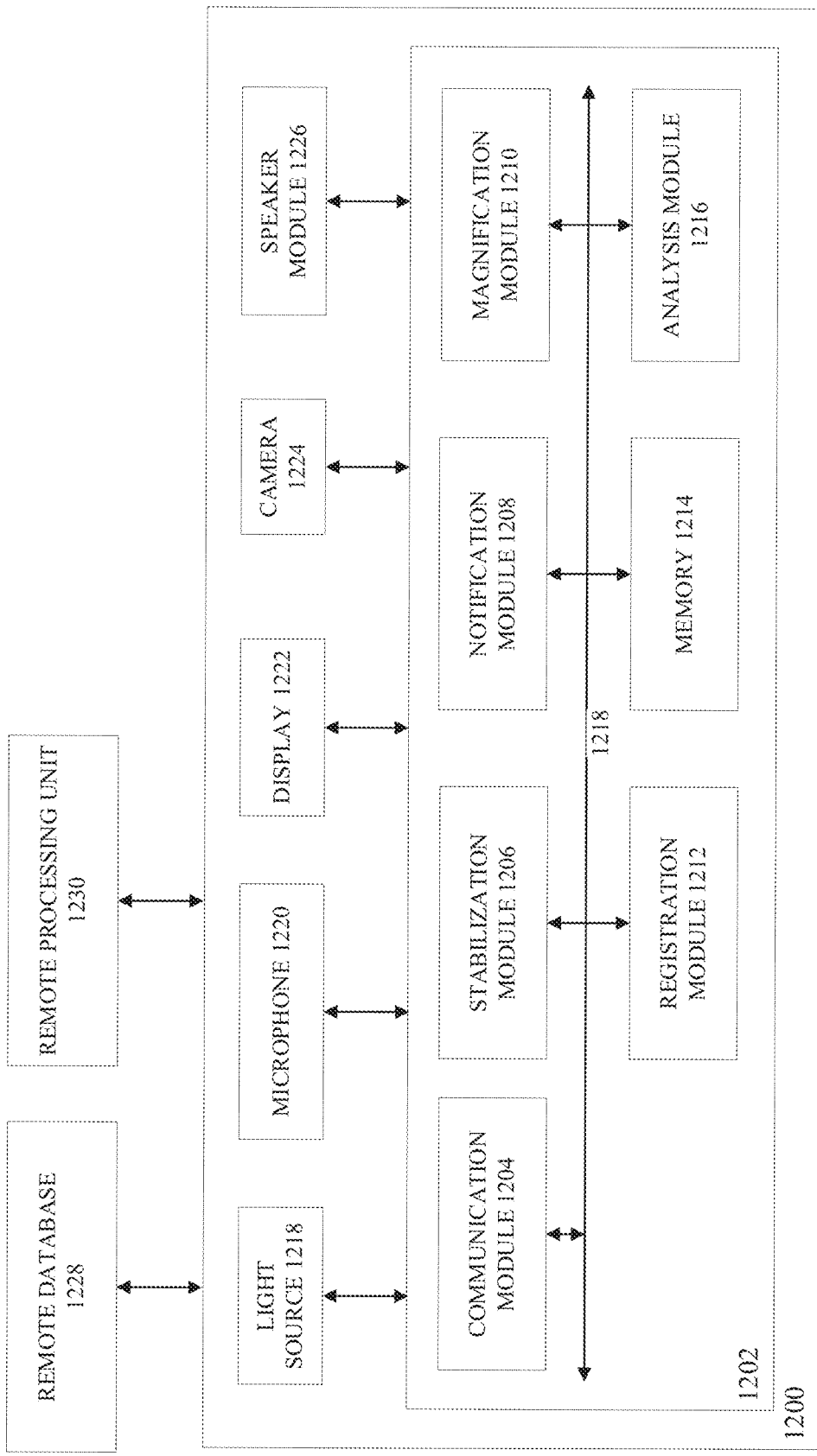
FIG. 12 illustrates a system according to an embodiment.

FIG. 12 illustrates a system according to an embodiment. The system 1200 includes at least a display 1222, at least one camera 1224, preferably at least one light source 1218, and a processor 1202, which may include at least one or more elements that are illustrated in the figure. The at least one camera 1224 is configured to capture at least one 2D image of an intraoral target area. The processor is configured to receive the captured at least one 2D image and process the received at least 2D image. Such processing may include determining, in relation to the gingiva margin, an insertion length of the probe tip in the periodontal pocket by applying an image processing technique on information obtained about a probe tip in the captured at least one 2D image. The determined insertion length represents the depth of the periodontal pocket. The display 1222 is configured to display the at least one 2D image and/or the real time image data. The display may also be configured to display a virtual content overlaid over the at least one 2D image and/or real time image data.

The processor may further include an analysis module that is configured to apply the image processing techniques to process the captured at least one 2D image and/or the real time image data. The image processing technique may utilize feature detection techniques that allows for detecting features and preferably object types of the at least one 2D image and/or real time image data from which at least one 2D image may be extracted.

The processor may further include at least one of the magnification module 1210 or stabilization module 1206. The magnification module 1210 is configured to apply a desired digital magnification and/or optical magnification to the real time image data or to the at least one 2D image captured by the at least one camera. The stabilization module 1206 is configured to apply digital stabilization to compensate for blur during/in the captured at least one 2D image and/or real time image data, for example blur introduced due to user's head movements and/or patient's jaw movement.

The processor may further include a memory 1214 that is configured to store digital data like patient record and provide digital data like providing digital probe profile and/or virtual content. The registration module 1212 is configured to receive the virtual content and overlay the virtual content over the real time image data such that at least a portion of the real time image data is viewable, through the overlaid content, on the display unit in real time. The analysis module utilizes registration techniques in order to obtain and/or maintain a spatial and/or temporal registration between the virtual content and real time image data.

The processor may further include additional elements such as computational module 1232 that be configured to perform one of more of tasks such as determining whether at least one of the timing criterion or local minima criterion is satisfied, updating guidelines, generating a depth profile, generating patient records with depth profile, determining whether the probe is in optimum orientation, generating a new visual guideline when local minima criterion is met, generating a patient record that includes depth profile, generating control commands for elements like camera or light etc., compressing the data before transmitting to the remote database or processing unit, or any other tasks disclosed herein.

The processor may also include a communication module 1204 that is configured to exchange data at least in one direction with at least one of a remote database 1228 or a remote processing unit 1230. The remote database and/or remote processing unit may be considered part of the system. The communication unit may receive data such as digital probe profile and/or virtual content from the remote database and send profile depth to the remote database. The communication module may also be configured to transmit a real time image data (preferably pre-processed real time image data) to the remote processing unit. The remote processing unit 1230 may be configured to perform further processing on the transmitted pre-processed image data received from the communication module.

The processor 1202 may also include a notification module 1208 that is configured to generate a notification for the user in different use scenarios. For example, the notification module would generate a notification for the user. The notification may relate to a specific procedural step or discrepancy. For example the processor may notify the user through an audio message delivered via the speaker module 1226 to "change the orientation and take a new measurement". The system may also include a microphone 1220 to receive the voice commands from the user and the computations module 1232 is configured to convert the received voice command into an instructions, representative of the voice command, that allow for a specific task such as storing the received verbal command in the patient record, changing magnification, etc.

FIG. 13A illustrates a probe element according to an embodiment. FIG. 13B illustrates the probe element of FIG. 13A in a displaced position according to an embodiment. The probe 1302 may include a force sensitive mechanism such as a spring mechanism that is operationally engaged with a probe element 1306. When the probe tip 1304 is pushed inside the pocket depth and a predefined insertion force is reached, the spring mechanism applies a force on the probe element that gets displaced/deviated (1306 being displaced in FIG. 13B), thus representing a variation of the probe element. The processor is configured to determine such variation, using image processing techniques, in the captured at least one 2D image and/or real time image date, indicating that the predefined insertion force for making pocket depth measurement is applied. The at least one 2D image captured where the processor determines such displacement (variation) of the probe element is usually used for determining the periodontal pocket depth. The processor may be configured to access the probe profile comprising a digital variation of a probe element when the predefined insertion force is applied; apply the image processing technique comprising assessing the information, from at least one 2D image, about the probe element in relation to the digital variation; and determine whether the predefined insertion force is applied. The digital variation may include geometrical information of the probe element when the variation occurs, and the processor may be configured to determine, based on a geometrical comparison, whether a match between the probe element identified from the at least one 2D image and the geometrical information exists. Additionally or alternatively, the digital variation may include an angular information between the displaced probe element and another part of the probe when the variation occurs, and the processor may be configured to determine whether a match between i) an angle 1308 that the probe element makes with another part of the probe 1310, as represented in the at least one 2D image, and ii) the angular information.

Figure 14A:
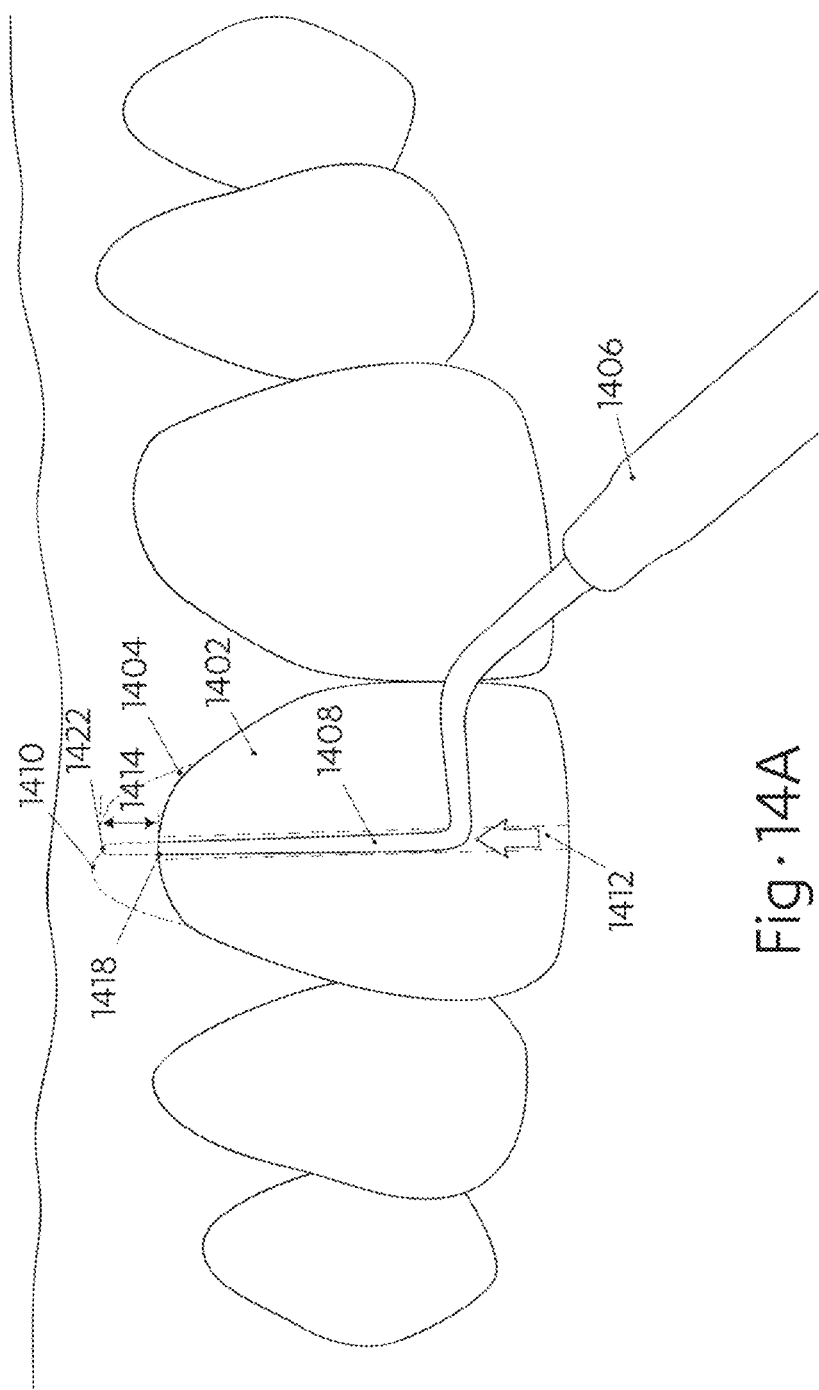
FIG. 14A illustrates a periodontal probe when in use for measuring a periodontal pocket having a local minima according to an embodiment.
Figure 14B:
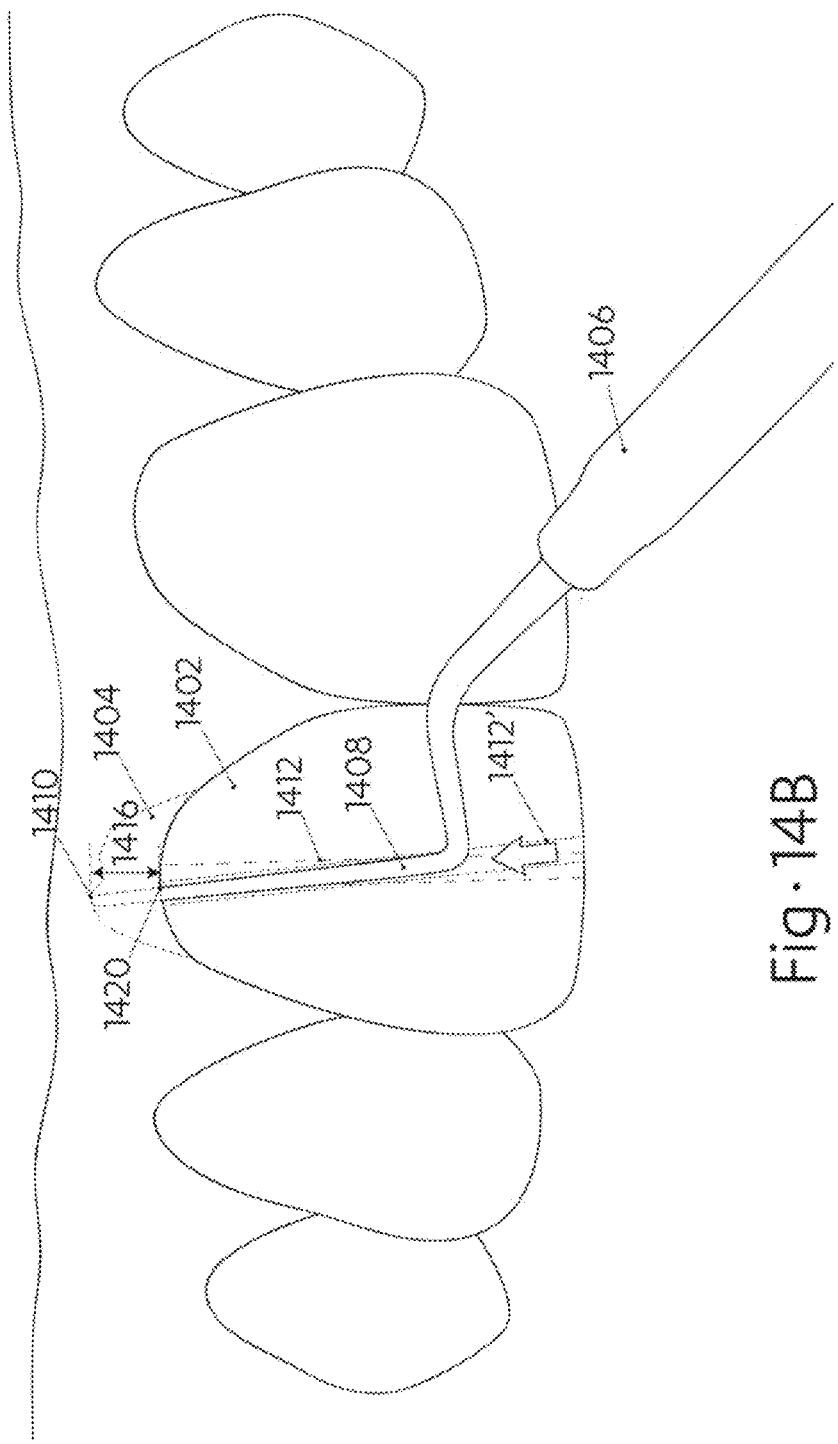
FIG. 14B illustrates the periodontal probe when in use for measuring the periodontal pocket having the local minima according to the embodiment of FIG. 14A.

FIG. 14A illustrates a periodontal probe when in use for measuring a periodontal pocket having a local minima according to an embodiment. FIG. 14B illustrates a periodontal probe when in use for measuring a periodontal pocket 1404 having a local minima according to the embodiment of FIG. 14A. The processor is configured to determine whether the probe tip 1408 of the probe 1406 in the real time image data 1400 comprising the tooth 1402 satisfies a local minima criterion, for example the probe tip in a sequence of 2D images meets the local minima criterion. The part of the probe tip and periodontal pocket shown in dashed line are not visible in the at least one 2D image and/or real time image data because such parts are sub-gingival features but are included here for illustration purpose only. The local minima criterion may include the probe tip 1408 representing maximum insertion length 1416 for a discrete measurement point 1420 when compared to the insertion length 1414 for measurement points 1418 in the neighborhood of the discrete measurement point. The range of neighboring measuring points along the gingiva margin may be predefined in the system or may be defined by the user. This may typically represent a situation when the epithelial attachment where the distal end of the probe sits (at 1422) during the measurement has an adjacent or proximal region 1410 where the epithelial attachment is more recessed defined by a local minima of the epithelial attachment (see 1422 relative to 1410). The processor may apply the image processing techniques to make the determination, for example by identifying the probe tip in the real time image data and determining in which of the 2D images of the sequence (representing real time image data), the length of the probe tip is the least visible outside the periodontal pocket, i.e. representing the maximum insertion length. The processor may further be configured to extract the at least one 2D image from the real time image data when the probe tip satisfies the local minima criterion and/or instruct the at least one camera to capture the at least one 2D image when the probe tip satisfies the local minima criterion. This approach allows for ensuring that the determined pocket depth is for a discrete point that is intended for the measurement.

The processor may further be configured to identify the discrete measurement point 1420 where the local minima criterion is satisfied, compare whether the identified discrete measurement point 1420 differs from the one or more points on the gingiva margin where pocket depth measurement is required such as the one or more points highlighted on the virtual content such as the three dimensional digital representation, and replacing the at least one of the one or more discrete points, e.g. highlighted points, on the gingiva margin with a point on the virtual content corresponding with the identified discrete measurement point 1420. The processor may further be configured to highlight the discrete measurement points on the gingiva margin in the represented virtual content for any future pocket depth measurement.

In an embodiment, the processor is configured to generate a new measurement guideline 1412', as part of the virtual content, corresponding to the discrete measurement point. The processor may further be configured to receive the new measurement guidelines 1412' and overlay the new measurement guideline over the real time image data such that at least a portion of the real time image data is viewable, through the overlaid new measurement guideline, on the display unit in real time. Accordingly, the guideline 1412 that correspond to a point where the probe tip 1408 of the probe 1406 in the real time image data 1400 comprising the tooth 1402 fails to satisfy a local minima criterion may be deleted.

Figure 15:
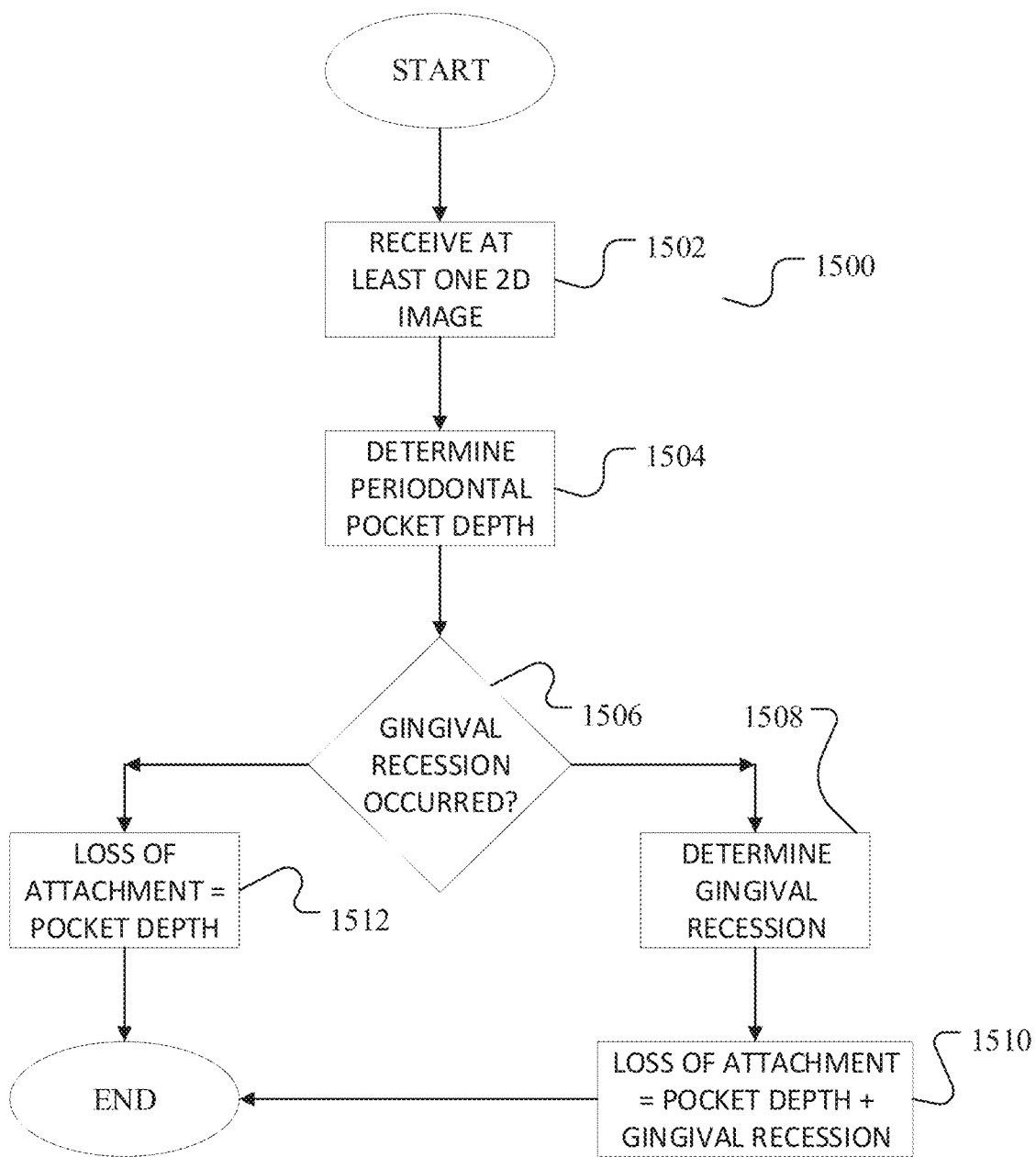
FIG. 15 illustrates a method for determining a loss of attachment.

FIG. 15 illustrates a method for determining a loss of attachment. The method 1500 receiving at 1502 at least one 2D image using at least one camera; determining, using an image processing technique on the at least one 2D image, i) at 1504, a periodontal pocket depth, ii) at 1506, whether a gingival recession has occurred, iii) at 1508, a gingival recession if the determination is made that the gingival recession has occurred, and iv) at 1510, the loss of attachment based on a combination of the determined periodontal pocket depth and the determined gingival recession. The determination of whether the gingival recession has occurred may be for a discrete point along the gingiva margin where the measurement is made and based on a distance between a cementoenamel junction and the gingiva margin. If, at 1506, the determination is made that no gingival recession has occurred, then the gingival recession is zero and the loss of attachment at 1512 equals to the determined pocket depth. The illustration recites a sequence of steps but the skilled person would realize that determination of the pocket depth may be made after the steps 1506 and 1508 (if gingival recession) has occurred.

Although some embodiments have been described and shown in detail, the disclosure is not restricted to such details, but may also be embodied in other ways within the scope of the subject matter defined in the following claims. In particular, it is to be understood that other embodiments may be utilized and structural and functional modifications may be made without departing from the scope of the present invention.

A claim may refer to any of the preceding claims, and "any" is understood to mean "any one or more" of the preceding claims.

It should be emphasized that the term "comprises/comprising/including" when used in this specification is taken to specify the presence of stated features, integers, operations, steps or components but does not preclude the presence or addition of one or more other features, integers, steps, components or groups thereof.

In claims enumerating several means, several of these means can be embodied by one and the same item of hardware. The mere fact that certain measures are recited in mutually different dependent claims or described in different embodiments does not indicate that a combination of these measures cannot be used to advantage.

The invention claimed is:

1. A system for measuring a depth of a periodontal pocket, the system comprising:
   a frame configured to be worn by a user;
   at least one camera, attached to the frame, configured to capture at least one 2D image of an intraoral target area, the at least one 2D image comprising a representation of at least:
      a part of the tooth,
      a gingiva margin defined by a section of the gingiva adjacent to the at least a part of the tooth, and
      a probe tip when the probe tip is inserted into a periodontal pocket; and
   a processor configured to receive the captured at least one 2D image and determine, in relation to the gingiva margin, an insertion length of the probe tip in the periodontal pocket by applying an image processing technique on information obtained about the probe tip in the captured at least one 2D image, wherein the determined insertion length represents a depth of the periodontal pocket.

2. The system according to claim 1, wherein the information obtained about the probe tip in the captured at least one 2D image comprises a digital representation of at least one of:
   at least one depth marker or fiducial marker comprised in the probe tip, visible outside the periodontal pocket; or
   geometrical information about the probe visible outside the periodontal pocket.

3. The system according to claim 2, wherein the processor is configured to apply the image processing technique to identify at least one of:
- a depth marker that is aligned or closest to the representation of the gingiva margin in the at least one 2D image; or
- fiducial markers that are visible in the at least one 2D image; or
- a specific viewpoint that is represented by the geometrical information about the probe.

4. The system according to claim 3, wherein the processor is configured to correlate at least one of:
- the identified depth marker that is aligned or closest to the representation of the gingiva margin in the at least one 2D image with a depth measurement, wherein correlating comprises comparing the identified depth marker with a probe profile indicating a length between a distal point of the probe tip and a plurality of depth markers of the probe tip; or
- the identified fiducial markers in the at least one 2D image with a depth measurement, wherein correlating comprises comparing the identified fiducial markers with a probe profile that represents the insertion length corresponding to the identified fiducial markers; or
- the identified geometrical information in the at least one 2D image with a depth measurement, wherein correlating comprises comparing the identified geometrical information with a probe profile that represents the insertion length corresponding to the identified geometrical information based on a non-overlapping section between the identified geometrical information and probe profile.

5. The system according to claim 3, wherein the processor is configured to:
- access the probe profile comprising a digital variation of a probe element when a predefined insertion force is applied;
- apply the image processing technique comprising assessing the information, from the at least one 2D image, about the probe element in relation to the digital variation; and
- determine whether the predefined insertion force is applied.

6. The system according to claim 3, wherein the processor is configured to:
- determine a correlation of one of the identified fiducial markers with a digital probe profile in order to determine an orientation of the probe; and
- determine whether the orientation of the probe is for a pocket depth measurement by comparing the identified fiducial marker with the visible fiducial marker(s).

7. The system according to claim 1, wherein the processor is configured to:
- receive a user instruction for manual indication of the tooth represented in the at least one 2D image or automatically identify the tooth represented in the at least one 2D image; and
- generate instructions for automatically recording the determined insertion length representing the pocket depth for the identified tooth in a digital patient record.

8. The system according to claim 1, wherein the processor is configured to create a depth profile for the tooth based on the determined insertion length representing the pocket depth, the depth profile comprising a collection of pocket depths at one or more points along the gingiva margin or along the entire length or a portion of the gingiva margin on a facial side or a lingual/palatal side of the tooth.

9. The system according to claim 1, wherein the at least one camera is configured to capture a real time image data and a stabilization module configured to apply digital image stabilization on the real time image data.

10. The system according to claim 9, further comprising a display; wherein:
- the at least one camera is configured to capture real-time image data of the intraoral target area comprising at least a part of the tooth, a gingiva margin defined by a section of the gingiva adjacent to the at least a part of the tooth, and a probe tip when the probe tip is inserted into the periodontal pocket, and
- the processor is configured to receive a three-dimensional digital representation of at least the part of the tooth and gingiva margin and overlaying the three-dimensional digital representation over the real time image data such that at least a portion of the real time image data is viewable, through the overlaid three-dimensional digital representation, on the display unit in real time.

11. The system according to claim 10, wherein the processor is configured to:
- automatically identify the tooth in the three-dimensional digital representation corresponding to the tooth for which the pocket depth is being measured; and
- highlight one or more points on the gingiva margin of the three-dimensional digital representation where pocket depth measurement is required.

12. The system according to claim 10, wherein the processor is configured to;
- automatically identify the tooth in the three-dimensional digital representation corresponding to the tooth for which the pocket depth is being measured; and
- digitally represent on the three-dimensional digital representation at least one historical pocket depth of the periodontal pocket at one or more discrete points or along the entire gingiva margin or a portion of the gingiva margin.

13. The system according to claim 9, wherein applying the digital image stabilization comprises;
- acquiring, using the at least one camera, a first image of the real time image data;
- acquiring, using the at least one camera, a second image of the real time image data, the second image being acquired at a later time than the first image;
- identifying corresponding feature points between the first image and second image, the corresponding feature points defining points that are tracked between the first image and second image; and
- transforming the second image using the identified corresponding feature points.

14. The system according to claim 9, further comprising a communication module configured to receive a virtual content from at least one of an integrated image source, a remote database, or a scanner unit; and
the processor is configured to:
- automatically align the virtual content with the real time image data, and
- automatically overlay the received virtual content over the real time image data of a target area such that at least a portion of the real time image data of the area is viewable, through the overlaid virtual content, on the display unit in real time.

15. The system according to claim 14, wherein the processor is configured to:
- receive information relating to movement of field of view of the at least one camera; and automatically align the virtual content with respect to the real time image data of the target area during and after the movement such that alignment between the virtual content and the real time image data is at least substantially maintained.

16. The system according to claim 14, wherein the processor is configured to
generate a measurement guideline, as part of the overlaid virtual content, corresponding to at least one discrete point; or
receive or generate a measurement guideline and overlay the measurement guideline over the real time image data such that at least a portion of the real time image data is viewable, through the overlaid measurement guideline, on the display unit in real time.

17. The system according to claim 16, wherein the processor is configured to apply magnification on at least a region of interest of the received real time image data, the magnification being a combination of a digital magnification and optical magnification.

18. The system according to claim 1, further comprising a second camera, wherein the at least one camera and the second camera are spatially separated from each other; and the processor is configured to apply stereo alignment between a real time image data acquired individually by the at least one camera and the second camera.

19. The system according to claim 18, wherein applying the stereo alignment comprises:
synchronizing the at least one camera and the second camera to individually capture real time image data at least substantially simultaneously;
acquiring, at least substantially simultaneously, a first current image using the at least one camera and a second current image using the second camera, the first current image and second current image corresponding to individually captured real time image data respectively;
identifying corresponding points between the first current image and second current image, the corresponding points defining points that are tracked between the first current image and second current image; and
transforming the second current image or the first current image using the identified corresponding points.

20. The system according to claim 1, wherein the processor is configured to:
identify a cementoenamel junction by applying the image processing technique;
determine a probe tip section, visible outside the pocket, that at least substantially aligns with the identified cementoenamel junction; and
determine attachment loss based on the probe tip section aligned with the cementoenamel junction.

21. The system according to claim 1, wherein the processor is configured to:
identify a cementoenamel junction by applying the image processing technique; and
determine a loss of attachment by calculating a combination of the determined insertion length and distance between a cementoenamel junction and a recessed gingiva margin.

22. The system according to claim 1, wherein:
the probe profile includes a digital specification such as geometrical information about the probe including different projected views of the probe when viewed from different perspectives; and
the processor is configured to compare the visible part of the probe with different projected views, and determine an orientation of the probe based on the matched projected view.

* * * * *